US008202834B2

(12) United States Patent
Fourney et al.

(10) Patent No.: US 8,202,834 B2
(45) Date of Patent: *Jun. 19, 2012

(54) FAT REGULATION

(75) Inventors: Patrick D. Fourney, Walnut Creek, CA (US); Volkmar Guenzler-Pukall, Emeryville, CA (US); Stephen J. Klaus, Boston, MA (US); Al Y. Lin, Castro Valley, CA (US); Thomas B. Neff, Atherton, CA (US); Todd W. Seeley, Oakland, CA (US)

(73) Assignee: FibroGen, Inc., San Francisco, CA (US)

( * ) Notice: Subject to any disclaimer, the term of this patent is extended or adjusted under 35 U.S.C. 154(b) by 170 days.

This patent is subject to a terminal disclaimer.

(21) Appl. No.: 12/589,229

(22) Filed: Oct. 19, 2009

(65) Prior Publication Data

US 2010/0168152 A1   Jul. 1, 2010

Related U.S. Application Data

(63) Continuation of application No. 10/729,167, filed on Dec. 4, 2003, now Pat. No. 7,618,940.

(60) Provisional application No. 60/476,726, filed on Jun. 6, 2003, provisional application No. 60/476,331, filed on Jun. 6, 2003, provisional application No. 60/431,351, filed on Dec. 6, 2002.

(51) Int. Cl.
*A61K 31/47* (2006.01)

(52) U.S. Cl. ......... 514/1.1; 514/292; 514/307; 514/312; 514/346; 435/375

(58) Field of Classification Search .................. None
See application file for complete search history.

(56) References Cited

U.S. PATENT DOCUMENTS

| | | | |
|---|---|---|---|
| 5,607,954 A | 3/1997 | Weidmann et al. | |
| 5,610,172 A | 3/1997 | Weidmann et al. | |
| 5,620,995 A | 4/1997 | Weidmann et al. | |
| 5,620,996 A | 4/1997 | Weidmann et al. | |
| 5,658,933 A | 8/1997 | Weidmann et al. | |
| 5,719,164 A | 2/1998 | Weidmann et al. | |
| 5,726,305 A | 3/1998 | Weidmann et al. | |
| 5,916,898 A * | 6/1999 | Edwards et al. | 514/292 |
| 5,942,434 A | 8/1999 | Ratcliffe et al. | |
| 6,020,350 A | 2/2000 | Weidmann et al. | |
| 6,093,730 A | 7/2000 | Weidmann et al. | |
| 6,124,131 A | 9/2000 | Semenza et al. | |
| 6,200,974 B1 | 3/2001 | Edwards et al. | |
| 6,432,927 B1 | 8/2002 | Gregory et al. | |
| 6,562,799 B1 | 5/2003 | Semenza | |
| 7,618,940 B2 * | 11/2009 | Fourney et al. | 514/1.1 |

FOREIGN PATENT DOCUMENTS

| | | |
|---|---|---|
| EP | 0650961 B1 | 3/1997 |
| EP | 0 878 480 * | 11/1998 |
| WO | WO-99/21860 A1 | 5/1999 |
| WO | WO 03/049686 * | 12/2002 |
| WO | WO-02/074981 A2 | 6/2003 |
| WO | WO-03/045440 A1 | 6/2003 |
| WO | WO-03/049686 A2 | 6/2003 |
| WO | WO-03/080566 A2 | 10/2003 |

OTHER PUBLICATIONS

Bruick, Richard K. and McKnight, Steven L., "A Conserved Family of Prolyl-4-Hydroxylases that Modify HIF," Science (2001) 294:1337-1340.
Epstein, Andrew C.R., et al., "C Elegans EGL-9 and Mammalian Homologs Define a Family of Dioxygenases that Regulate HIF by Prolyl Hydroxylation," Cell (2001) 107:43-54.
Fushiki, T. and Kano, T., "Effects of Chronic Hypoxia on the Whole-Body Insulin Action in Rats," Can J Physiol Pharmacol (1992) 70:1522-1524.
Gunga, Hanns C., et al., "Austrian Moderate Altitude Study (AMAS 2000)—Fluid Shifts, Erthyropoiesis and Angiogenesis in Patients with Metabolic Syndrome at Moderate Altitude (~=1700 m)," Eur J Appl Physiol (2003) 88:497-505.
Ivan, Mircea, et al., "HIFα Targeted for VHL-Mediated Destruction by Proline Hydroxylation: Implications for O2 Sensing," Science (2001) 292:464-468.
Jaakkola, Panu, et al., "Targeting of HIFα to the von Hippel-Lindau Ubiquitylation Complex by O2-Regulated Prolyl Hydroxylation," Science (2001) 292:468-472.
Srinivas, Vickram, et al., "Characterization of an Oxygen/Redox-Dependent Degradation Domain of Hypoxia-Inducible Factor α (HIF-α) Proteins," Biochem Biophys Res Comm (1999) 260:557-561.
Yun, Zhong, et al.,."Inhibition of PPARγ2 Gene Expression by the HIF-1-Regulated Gene DEC1/Stra13: A Mechanism for Regulation of Adipogenesis by Hypoxia," Dev Cell (2002) 2(3):331-341.

* cited by examiner

*Primary Examiner* — Christopher R. Tate
*Assistant Examiner* — Roy Teller
(74) *Attorney, Agent, or Firm* — Leanne C. Price, Esq.; Paul E. Borchardt

(57) ABSTRACT

The present invention provides methods and compounds for regulating fat metabolism and achieving fat homeostasis in a subject. Methods and compound for regulating body weight, reducing body fat, and inducing weight loss are also provided, as are methods and compounds for treating or preventing obesity and for preventing or treating conditions associated with altered fat metabolism including, e.g., obesity, diabetes, atherosclerosis, etc.

27 Claims, 11 Drawing Sheets

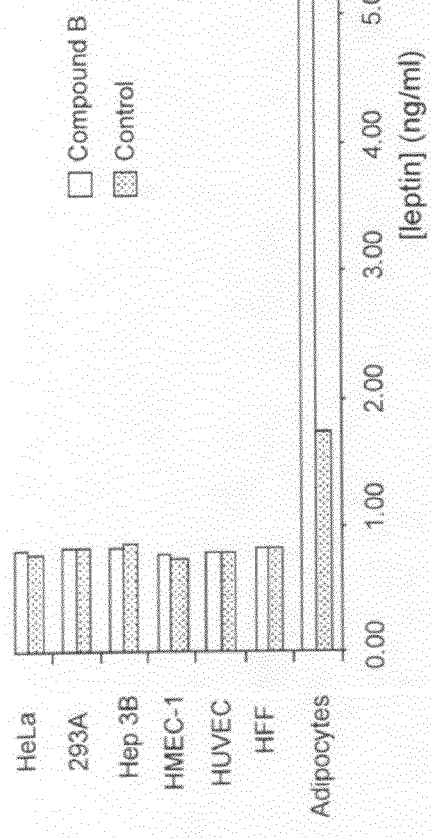
FIG. 1A
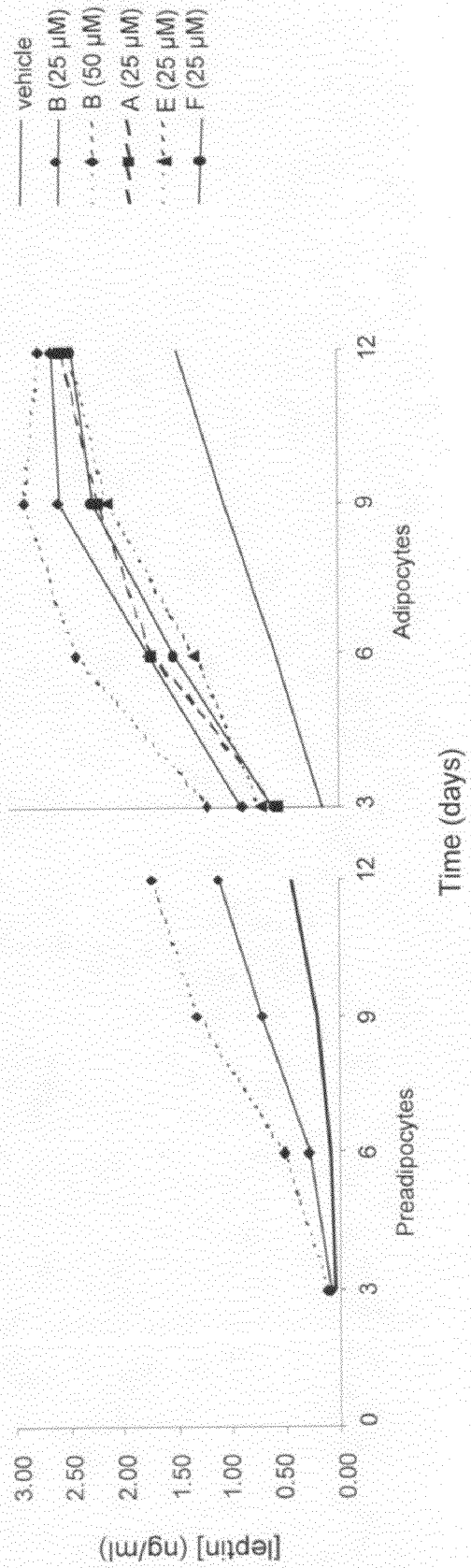
FIG. 1B
FIG. 1C 20 mg/kg compound B 100 mg/kg compound B FIG. 9A
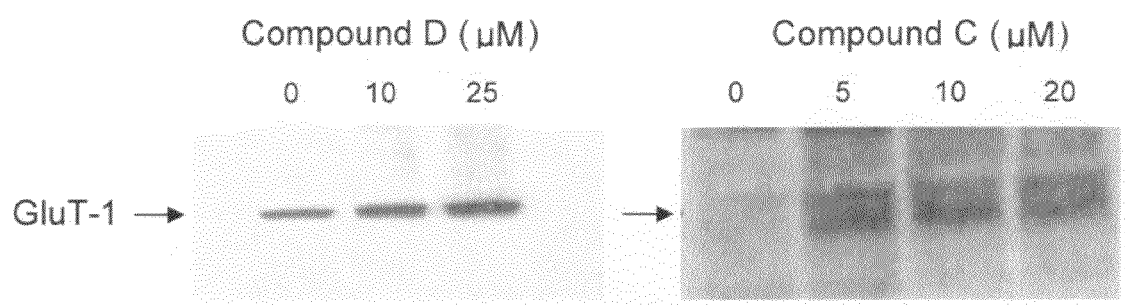
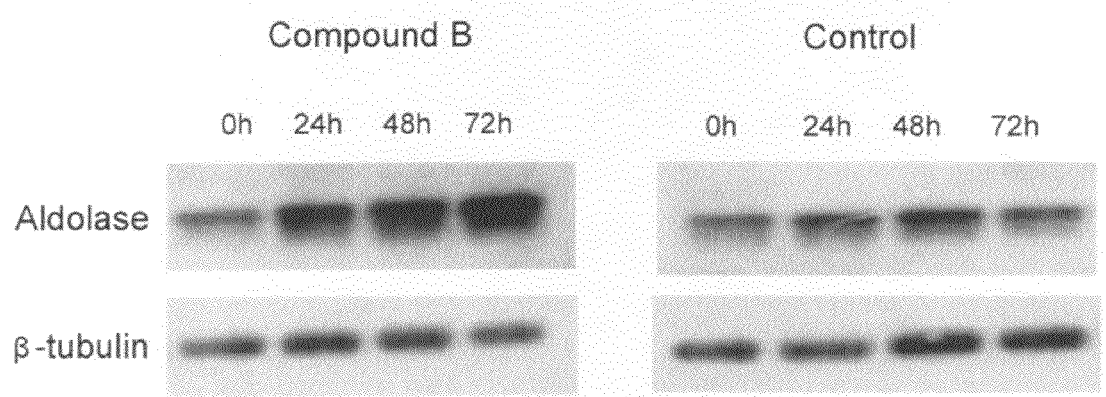
FIG. 9B

SEQUENCE LISTING

```
<160> NUMBER OF SEQ ID NOS: 1

<210> SEQ ID NO 1
<211> LENGTH: 19
<212> TYPE: PRT
<213> ORGANISM: Homo sapiens

<400> SEQUENCE: 1

Asp Leu Asp Leu Glu Met Leu Ala Pro Tyr Ile Pro Met Asp Asp Asp
1               5                   10                  15

Phe Gln Leu
```

FAT REGULATION

This application claims the benefit of U.S. application Ser. No. 10/729,167, filed 4 Dec. 2003; U.S. Provisional Application Ser. No. 60/431,351, filed on 6 Dec. 2002; U.S. Provisional Application Ser. No. 60/476,331, filed on 6 Jun. 2003; and U.S. Provisional Application Ser. No. 60/476,726, filed on 6 Jun. 2003, each of which is incorporated by reference herein in its entirety.

FIELD OF THE INVENTION

The present invention relates to fat homeostasis and metabolism and to regulation of body weight.

BACKGROUND OF THE INVENTION

Obesity, typically defined as a body mass index (BMI) of 30 or above, is a major health issue, especially in the industrialized world. Obesity currently affects an estimated 250 million adults, a number expected to grow substantially as overweight adolescents mature into obese adults. As noted above, obesity is associated with many adverse health effects, including an increased risk of diabetes and heart disease. Abdominal obesity, the distribution of excess adipose tissue in the abdominal region, has in particular been shown to correlate with diabetes and heart disease, e.g., the metabolic syndrome. Excess fat is correlated with increased chance of heart attack, stroke, or other types of cardiovascular disease; high blood pressure, high cholesterol, diabetes; cancer including postmenopausal breast cancer and cancer of the endometrium, colon, and kidney; arthritis, gallstones, sleep apnea, and adult onset asthma. There is thus a need in the art for effective means of regulating fat metabolism and the encompassed processes in order to achieve weight loss, and to minimize the risk of the development or progression of correlative conditions.

In view of the numerous deleterious conditions associated with altered or impaired fat metabolism and fat homeostasis, and the increasing frequency of obesity and unregulated weight gain, there is a need for methods for regulating fat metabolism. Further, there is a need in the art for methods of regulating body weight by regulating fat production, utilization, and storage. In addition, there is a need in the art for methods and compounds for treatment of obesity.

SUMMARY OF THE INVENTION

The present invention relates to methods and compounds for regulating fat metabolism, achieving fat homeostasis, regulating body weight, reducing fat stores, and inducing weight loss in a subject. Methods and compounds for treating or preventing obesity, including diet-induced obesity, obesity associated with diabetes, etc., are also provided.

In various embodiments, the subject is a cell, tissue, or organ. In other embodiments, the subject is an animal, preferably a mammal, most preferably a human. When the subject is a cell, the invention specifically contemplates that the cell can be an isolated cell, either prokaryotic or eukaryotic. In the case that the subject is a tissue, the invention specifically contemplates both endogenous tissues and in vitro tissues, e.g., tissues grown in culture. In preferred embodiments, the subject is an animal, particularly, an animal of mammalian species including rat, rabbit, bovine, ovine, porcine, murine, equine, and primate species. In a most preferred embodiment, the subject is human.

The present invention provides methods for regulating fat metabolism in a subject. In one aspect, the present methods comprise regulating fat metabolism in a subject by stabilizing HIFα in the subject, thus regulating fat metabolism in the subject. In various aspects, HIFα is HIF-1α, HIF-2α, or HIF-3α. In a preferred aspect, stabilizing HIFα comprises administering to the subject an effective amount of a compound that inhibits HIF hydroxylase activity, thus stabilizing HIFα.

Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. In other aspects, the present invention contemplates that stabilizing HIFα comprises administering an agent that stabilizes HIFα. The agent can be composed of polynucleotides; polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

The invention further contemplates methods for regulating fat metabolism in a subject by administering to the subject an effective amount of a compound of the invention, thus regulating fat metabolism in the subject. In one aspect, a compound of the invention is a compound that inhibits HIF hydroxylase activity. In a preferred aspect, a compound of the invention is a compound that inhibits HIF prolyl hydroxylase activity. In another preferred aspect, the HIF hydroxylase is selected from the group consisting of EGLN1, EGLN2, and EGLN3.

The invention further provides methods for regulating a fat metabolic process in a subject by stabilizing HIFα in the subject, or by administering to the subject an effective amount of a compound of the invention, thereby regulating the fat metabolic process in the subject. In various embodiments, the fat metabolic process is selected from the group consisting of, e.g., fat uptake, fat transport, fat storage, fat processing, fat utilization, and fat synthesis.

In particular embodiments, the present invention contemplates methods for altering expression of a fat regulatory factor in a subject by stabilizing HIFα in the subject, or by administering to the subject an effective amount of a compound of the invention, thereby altering expression of the fat regulatory factor in the subject.

In one embodiment, the present invention provides a method for increasing expression of a fat regulatory factor in a subject, by stabilizing HIFα in the subject or by administering to the subject an effective amount of a compound of the invention, thereby increasing expression of the fat regulatory factor in the subject. In further embodiments, the fat regulatory factor is selected from the group consisting of leptin, apolipoprotein A-IV, cytosolic acyl CoA thioesterase-1, insulin-like growth factor binding protein (IGFBP)-1, carnitine acetyl transferase, and PAI-1. In a particular aspect, the increase in expression of the fat regulatory factor is a sustained increase.

Methods for altering expression of adipogenic factors is further contemplated. In one embodiment, the invention encompasses methods for increasing expression of DEC1/Stra13 in a subject, the method comprising stabilizing HIFα in the subject or administering to the subject an effective amount of a compound of the invention, thereby increasing expression of DEC1/Stra13 in the subject. In another embodiment, the invention provides methods for decreasing expression of peroxisome proliferator activated receptor (PPAR)-γ in a subject, the method comprising stabilizing HIFα in the subject or administering to the subject a compound of the invention, thereby decreasing expression of PPAR-γ in the subject.

The present invention provides methods for achieving fat homeostasis in a subject. In one aspect, the present methods comprise achieving fat homeostasis in a subject by stabilizing HIFα in the subject, thereby achieving fat homeostasis in the subject. In another aspect, the present methods comprise achieving fat homeostasis in a subject by administering to the subject an effective amount of a compound of the invention, thereby achieving fat homeostasis in the subject.

The present invention provides methods for regulating body weight in a subject. In one aspect, the present methods comprise regulating body weight in a subject by stabilizing HIFα in the subject, thereby regulating body weight in the subject. In another aspect, the present methods comprise regulating body weight in a subject by administering to the subject an effective amount of a compound of the invention, thereby regulating body weight in the subject.

The present invention provides methods for reducing body fat in a subject. In one aspect, the present methods comprise reducing body fat in a subject by stabilizing HIFα in the subject, thereby reducing body fat in the subject. In another aspect, the present methods comprise reducing body fat in a subject by administering to the subject an effective amount of a compound of the invention, thereby reducing body fat in the subject. In various aspects, the body fat is accumulated or deposited fat, and the reduction is a decrease in stored fat (i.e., fat stores). In other aspects, the methods are applied to prevent accumulation or deposition of fat, e.g., preventing an increase in stored fat. In further aspects, the body fat is visceral or abdominal fat.

The present invention provides methods for inducing weight loss in a subject. In one aspect, the present methods comprise inducing weight loss in a subject by stabilizing HIFα in the subject, thereby inducing weight loss. In another aspect, the present methods comprise inducing weight loss in a subject by administering to the subject an effective amount of a compound of the invention, thereby inducing weight loss. In a preferred aspect, a compound of the invention is a compound that inhibits HIF hydroxylase activity. In one embodiment, the invention provides methods for inducing weight loss in a subject without concomitant muscle loss. In certain embodiments, the weight loss is dose-dependent.

The present invention provides methods for treating or preventing obesity in a subject. In one aspect, the present methods comprise treating or preventing obesity in a subject by stabilizing HIFα in the subject, thereby treating or preventing obesity. In another aspect, the present methods comprise treating or preventing obesity in a subject by administering to the subject an effective amount of a compound of the invention, thereby treating or preventing obesity. In certain aspects, it is contemplated that the obesity is diet-induced obesity. In other aspects, the obesity is associated with diabetes, e.g., obesity as a risk factor for development of diabetes, or obesity that develops with or as a result of progression of the disease.

The present invention provides methods for reducing oxygen consumption in a subject. In one aspect, the present methods comprise reducing oxygen consumption in a subject by stabilizing HIFα in the subject, thereby reducing oxygen consumption in the subject. In another aspect, the present methods comprise reducing oxygen consumption in a subject by administering to the subject an effective amount of a compound of the invention, thereby reducing oxygen consumption in the subject. In certain embodiments, the methods of the invention reduce oxygen demand of the subject. In various embodiments, the subject is a cell, tissue, organ, multi-organ system, or whole organism, including an animal, preferably a mammal, most preferably a human. Further, the methods of the invention can be used, for example, to reduce the demand for oxygen and increase metabolic efficiency in cells grown in culture.

In one embodiment, the present invention provides methods for generating energy in a subject under low oxygen conditions. In a further embodiment, the present invention provides methods for inducing a metabolic shift in oxygen consumption, e.g., reducing oxygen consumption. Methods for minimizing oxygen consumption required to achieve and to maintain varying levels of exertion are specifically contemplated. These methods can be particularly useful in applications involving elevated levels of exertion, e.g., athletic pursuits, physical exertion, e.g., under water, at high altitude, under conditions of severe stress, e.g., battlefield conditions, etc.

The above methods specifically contemplate use of a compound of the invention. In certain aspects, a compound of the invention is selected from the group consisting of compounds A, B, C, D, E, F, G, and H. In one aspect, the compound is a 2-oxoglutarate dioxygenase mimetic. In a further aspect, the 2-oxoglutarate dioxygenase mimetic is a substituted heterocyclic carboxamide. The invention specifically contemplates embodiments in which the substituted heterocyclic carboxamide is selected from the group consisting of quinolines, isoquinolines, phenanthrolines, pyridines, pyrimidines, β-carbolines, etc.

In various embodiments, the present invention provides formulations or medicaments or pharmaceutical compositions comprising the compounds of the invention, and methods for the manufacture and use of such formulations or medicaments or pharmaceutical compositions.

In one embodiment, the invention encompasses methods for treating or preventing a condition associated with impaired fat homeostasis in a subject having such a condition, the method comprising stabilizing HIFα in the subject or comprising administering to the subject an effective amount of a compound of the invention, thereby treating or preventing the condition in the subject. In various embodiments, the condition associated with impaired fat homeostasis is obesity, including diet-induced obesity; genetically-induced obesity; obesity that results from or develops in association with certain therapeutic treatments, e.g., insulin-based therapies, etc.; hyperlipidemia; hypolipidemia; cholesterolemia; or atherosclerosis.

In one embodiment, the invention encompasses methods for treating or preventing a condition associated with impaired fat metabolism in a subject having such a condition, the method comprising stabilizing HIFα in the subject or administering to the subject an effective amount of a compound of the invention, thereby treating or preventing the condition in the subject. In various embodiments, the condition associated with impaired fat homeostasis is obesity, including diet-induced obesity, genetically-induced obesity, obesity that results from or develops in association with certain therapeutic treatments, e.g., insulin-based therapies, etc.; hyperlipidemia; hypolipidemia; cholesterolemia; atherosclerosis; etc.

These and other embodiments of the subject invention will readily occur to those of skill in the art in light of the disclosure herein.

BRIEF DESCRIPTION OF THE DRAWINGS

FIGS. 1A, 1B, and 1C show levels of leptin in human cell culture media following treatment with various compounds of the invention. Cell lines shown in the figure are preadipocytes, adipocytes, human foreskin fibroblasts (HFF), human microvascular endothelial cells (HMEC-1), human umbilical vein endotheial cells (HUVEC), human hepatocellular carcinoma cells (Hep 3B), adenovirus-transformed fetal kidney epithelium cells (293A), and cervical epithelial carcinoma cells (HeLa).

FIG. 2A shows expression of various fat metabolism genes, including apolipoprotein A-IV, acyl CoA thioesterase, carnitine acetyl transferase, and insulin-like growth factor binding protein (IGFBP)-1. FIG. 2B shows expression of the plasminogen activator inhibitor (PAI)-1 gene.

FIG. 3A shows changes in expression of DEC1/Stra13 over time following treatment with a compound of the invention. FIG. 3B shows increased expression of DEC1/Stra13 in several tissues following treatment. FIG. 3C shows decreased expression of peroxisome proliferator activated receptor (PPAR)-γ following treatment with compounds of the invention.

FIG. 4A shows dose-dependent retardation in weight gain in animals treated with a compound of the invention. FIG. 4B shows that the weight loss in animals is not due to loss of muscle and/or vital organ weight, as exemplified by the heart.

FIGS. 9A and 9B show induction of glucose transporter-1 (GluT-1) and aldolase in cells treated with compounds of the invention.

DESCRIPTION OF THE INVENTION

Figure 2A:
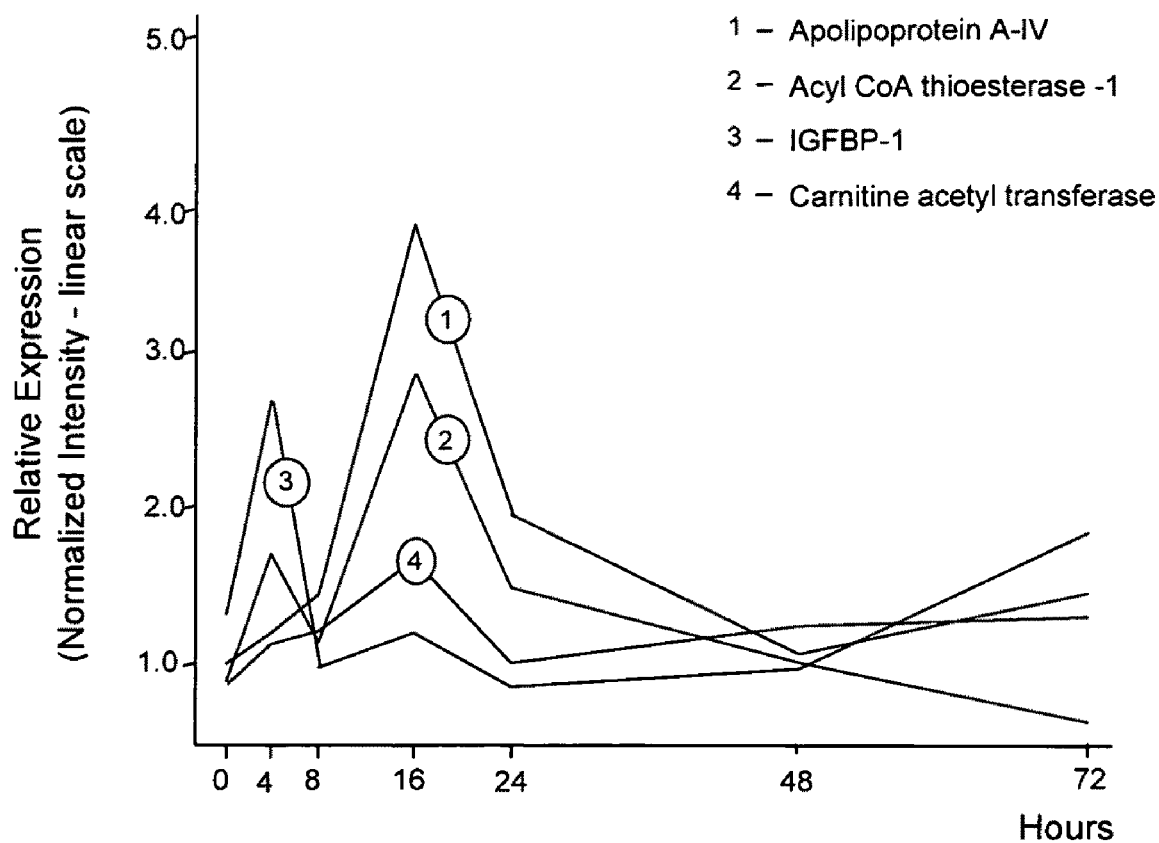
FIGS. 2A and 2B show increase in expression of genes encoding proteins involved in fat metabolism and distribution in liver of animals treated with a compound of the invention.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to "a compound" is a reference to one or more compounds and to equivalents thereof as described herein and as known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

DEFINITIONS

The terms "fat regulation" and "regulating fat metabolism" encompass processes by which a cell, tissue, organ, organ system, or whole organism achieves and/or maintains fat homeostasis by altering, e.g., increasing or decreasing, specific aspects of fat metabolism. Fat metabolism encompasses processes whereby fats such as triglycerides, fatty acids, cholesterol, lipids, and phospholipids, are synthesized, transported, taken up, processed, utilized, or stored. Specific aspects of fat metabolism and regulation include expression of lipoproteins or enzymes which facilitate transport and movement of fat in the blood, and retention or secretion of fat by a cell; alteration in expression and/or activity of enzymes involved in fat utilization or formation, including, e.g., lipolytic and lipogenic enzymes such as acyltransferases, oxidases, lipoxygenases, etc.; and alteration of fat distribution within the body, e.g., in or around tissues, fat pads, etc.; or body fluids, including, e.g., interstitial (i.e. extracellular) and intracellular fluids, blood, urine, and the like.

The terms "metabolic condition" and "metabolic disorder" are used interchangeably and refer to any disorder associated with or aggravated by altered fat regulation. Such disorders include, but are not limited to, atherosclerosis, heart disease, and obesity.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between 18.5 and 24.9 is considered normal, whereas a BMI between 25.0 and 29.9 is considered overweight, a BMI at or above 30.0 is considered obese, and a BMI at or above 40 is considered morbidly obese. (See, e.g., Gallagher et al. (2000) Am J Clin Nutr 72:694-701.) These BMI ranges are based on the effect of body weight on increased risk for disease. Some common conditions related to overweight and obesity include cardiovascular disease, high blood pressure, osteoarthritis, cancer, and diabetes mellitus. Although BMI correlates with body fat, the relation between BMI and actual body fat differs with age and gender. For example, women are more likely to have a higher percent of body fat than men for the same BMI.

Another measure of obesity is body-fat percentage. Various methods are available for indirectly measuring body fat, including skin-fold measurement, hydrodensitometry, bioelectrical impedance analysis (BIA), dual-energy X-ray absorptiometry, total-body potassium measurement, and in vivo neutron activation analysis. Hydrodensitometry, or hydrostatic weighing (HW), determines total body volume by measuring the difference between a subject's weight in water and in air. Similarly, air-displacement plethysmography (AP) determines total body volume by measuring the reduction in chamber volume caused by introducing a subject into a chamber with a fixed air volume. Whole-body density and body composition are then calculated using validated prediction equations. BIA estimates body resistance, or impedance, from a voltage drop initiated from a small current passed between electrodes. The level of impedance, an indication of the water and electrolyte composition of the body, is then used to estimate lean tissue content and body water volume from developed regression equations. Assuming a hydration fraction of lean tissue, additional regression equations are used to estimate lean body mass and fat mass. The percentage of body fat in women should generally be about 17 to 27 percent, although up to 31 percent is considered acceptable. In men, the body fat percentage should generally be 10 to 20 percent, although up to 25 percent is considered acceptable.

The term "HIFα" refers to the alpha subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α(Genbank Accession No. AAD22668); murine HIF-1α (Genbank Accession No. Q61221), HIF-2α (Genbank Accession No. BAA20130 and AAB41496), and HIF-3α(Genbank Accession No. AAC72734); rat HIF-1α (Genbank Accession No. CAA70701), HIF-2α (Genbank Accession No. CAB96612), and HIF-3α(Genbank Accession No. CAB96611); and cow HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

Fragments of HIFα include the regions defined by human HIF-1α from amino acid 401 to 603 (Huang et al., supra), amino acid 531 to 575 (Jiang et al. (1997) J Biol Chem 272:19253-19260), amino acid 556 to 575 (Tanimoto et al., supra), amino acid 557 to 571 (Srinivas et al. (1999) Biochem Biophys Res Commun 260:557-561), and amino acid 556 to 575 (Ivan et al. (2001) Science 292:464-468). Further, a fragment of HIFα includes any fragment containing at least one occurrence of the motif LXXLAP, e.g., as occurs in the HIF-1α native sequence at $L_{397}$TLLAP and $L_{559}$EMLAP. Additionally, a fragment of HIFα includes any fragment retaining at least one functional or structural characteristic of HIFα. For example, a HIF peptide for use in the screening assay of Example 9 may comprise DLDLEMLAPYIPMDDDFQL (SEQ ID NO:1).

The term "HIF hydroxylase" refers to any enzyme that is capable of hydroxylating an amino acid residue in the HIF protein, particularly the HIFα subunit. Preferably, the amino acid residue is a proline and/or an asparagine residue.

The term "HIF asparaginyl hydroxylase" refers to any enzyme that is capable of hydroxylating an asparagine residue in the HIF protein. Preferably, the asparagine residue hydroxylated by HIF asparaginyl hydroxylase includes, e.g., the $N_{803}$ residue of HIF-1α or a homologous asparagine residue in another HIFα isoform. HIF asparaginyl hydroxylase includes Factor Inhibiting HIF (FIH), an asparaginyl hydroxylase responsible for regulating transactivation of HIFα (GenBank Accession No. AAL27308; Mahon et al. (2001) Genes Dev 15:2675-2686; Lando et al. (2002) Science 295:858-861; and Lando et al. (2002) Genes Dev 16:1466-1471. Also, see, Elkins et al. (2002) J Biol Chem C200644200.)

The terms "HIF prolyl hydroxylase" and "HIF-PH" refer to any enzyme that is capable of hydroxylating a proline residue in the HIF protein. Preferably, the proline residue hydroxylated by HIF-PH includes the proline found within the motif LXXLAP, e.g., as occurs in the human HIF-1α native sequence at $L_{397}$TLLAP and $L_{559}$EMLAP. HIF-PH includes members of the Egl-9 (EGLN) gene family described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). Examples of HIF-PH enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF-PH may include *Caenorhabditis elegans* EGL-9 (GenBank Accession No. AAD56365) and *Drosophila melanogaster* CG1114 gene product (GenBank Accession No. AAF52050). HIF-PH also includes any active fragment of the foregoing full-length proteins.

The term "sample" can refer to any material obtained either directly or indirectly from a subject. Samples may be obtained or derived, for example, from bodily fluids, secretions, tissues, cells, or cells in culture including, but not limited to, saliva, blood, urine, serum, plasma, vitreous, synovial fluid, cerebral spinal fluid, amniotic fluid, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. Samples may be derived from any source, such as, for example, a human subject, or a non-human mammalian subject, etc. Also contemplated are samples derived from any animal model of disease. A sample can be in solution or can be, for example, fixed or bound to a substrate. A sample can refer to any material suitable for testing for the presence of transcripts or proteins associated with metabolic regulation; or for measuring fat and glucose levels. Methods for obtaining such samples are within the level of skill in the art.

The term "subject" can refer to isolated cells, either prokaryotice or eukaryotic, or tissues grown in culture; or, more preferably, subject refers to animals, particularly a mammalian species including rat, rabbit, bovine, ovine, porcine, murine, equine, and primate, particularly human.

Invention

The present invention provides methods and compounds for regulating fat metabolism and achieving fat homeostasis, and for treating or preventing or minimizing the risk of developing conditions associated with altered or impaired fat homeostasis and metabolism. Such conditions include, but are not limited to, obesity and the like. Methods and compounds for regulating levels of stored fat; for maintaining or decreasing body weight; and for regulating fat processing, uptake, transport, storage, synthesis, utilization, and distribution are also provided herein. The invention specifically provides methods for treating or preventing obesity, e.g., preventing or reducing weight gain and/or inducing fat loss. In one aspect, this is accomplished by pharmacologically inducing a metabolic shift toward the use of fat and/or fatty acids as a primary energy source for cells.

The invention relates to the discovery that stabilization of the alpha subunit of hypoxia inducible factor (HIFα) leads to a decrease in fat deposition and that stabilization of HIFα regulates fat metabolism. The invention further provides methods and compounds that decrease adipose tissue formation and fat deposition and effectively regulate processes of fat metabolism, e.g., fat transport, uptake, processing, utilization, storage, etc.

Hypoxia inducible factor (HIF) is involved in the response of cells, tissues, and organs to reduced oxygen, i.e., hypoxia. Exposure to hypoxia, e.g., at high altitude, is known to cause loss of appetite and weight loss. (See, e.g., Fushiki et al. (1992) Can J Physiol Pharmacol 70:1522-1524; Gunga et al. (2003) Eur J Appl Physiol 88:497-505; and Tschop and Morrison (2001) In: *Hypoxia: From genes to the bedside* (R C Roach et al., Eds.), Kluwer Academic/Plenum Publishers, New York, N.Y.) HIFα is degraded under normoxic, i.e., normal oxygen conditions, and is stabilized under hypoxic, i.e., low oxygen conditions. Upon stabilization, HIFα combines with HIFβ to produce a number of downstream effects. It was recently determined that hydroxylation of particular residues on the HIFα subunit targeted HIFα for degradation, thus preventing formation of stable HIF complex under normal oxygen conditions, and that the hydroxylation was determined to result from the activity of certain HIF hydroxylase enzymes. (See, e.g., Ivan et al. (2001) Science 292:464-468; Jaakkola et al. (2001) Science 292:468-472; Epstein et al. (2001) Cell 107:43-54; and Bruick and McKnight (2001) Science 294:1337-1340.) These HIF hydroxylase enzymes belong to the 2-oxoglutarate dioxygenase enzyme family. These enzymes are oxygen-dependent and, under low oxygen (i.e., hypoxic) conditions, the hydroxylation of HIFα residues is inhibited. Therapeutic stabilization of HIFα and stabilization of HIFα through inhibition of hydroxylation of HIFα have been previously described. (See, e.g., International Publication No. WO 03/049686, incorporated herein by reference in its entirety.)

Methods

In one aspect, the present invention provides methods for decreasing adipose tissue formation and fat deposition, mobilizing fat stores, regulating fat metabolism, and achieving fat homeostasis by stabilizing HIFα in a subject. In a further aspect, the methods comprise decreasing adipose tissue formation and fat deposition, mobilizing fat stores, regulating fat metabolism, and achieving fat homeostasis by inhibiting the hydroxylation of HIFα in a subject. In a preferred aspect, the methods of the present invention encompass decreasing adipose tissue formation and fat deposition, mobilizing fat stores, regulating fat metabolism, and achieving fat homeostasis by inhibiting the activity of at least one HIF hydroxylase enzyme in a subject. In a most preferred aspect, the methods comprise decreasing adipose tissue formation and fat deposition, mobilizing fat stores, regulating fat metabolism, and achieving fat homeostasis by inhibiting the activity of a HIF prolyl hydroxylase enzyme.

Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. (See, e.g., U.S. Pat. Nos. 6,562,799 and 6,124,131; and U.S. Pat. No. 6,432,927.) In other aspects, the present invention contemplates that stabilizing HIFα comprises administering an agent that stabilizes HIFα. The agent can be composed of polynucleotides, e.g. antisense sequences (see, e.g., International Publication No. WO 03/045440); polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

In other embodiments, the methods of the invention comprise stabilizing HIFα by inhibiting the activity of at least one enzyme selected from 2-oxoglutarate dioxygenase family members. In a preferred embodiment, the enzyme is a HIF hydroxylase enzyme, e.g., EGLN-1, EGLN-2, EGLN-3, FIH, etc. (See, e.g., Taylor (2001) Gene 275:125-132; Epstein et al. (2001) supra; Bruick and McKnight, supra; Mahon et al., supra; and Lando et al., supra.) It is specifically contemplated, however, that the enzyme be any enzyme selected from the 2-oxoglutarate dioxygenase family, including, for example, procollagen lysyl hydroxylase (LH)-1, -2, and -3; procollagen prolyl 3-hydroxylase, procollagen prolyl 4-hydroxylase α(I) and α(II), thymine 7-hydroxylase, aspartyl(asparaginyl) ε-hydroxylase, ε-N-trimethyllysine hydroxylase, and γ-butyrobetaine hydroxylase, etc. (See, e.g., Majamaa et al. (1985) Biochem J 229:127-133; Myllyharju and Kivirikko (1997) EMBO J 16:1173-1180; Thornburg et al. (1993) 32:14023-14033; and Jia et al. (1994) Proc Natl Acad Sci USA 91:7227-7231.)

In certain embodiments, the methods comprise decreasing adipose tissue formation and fat deposition, mobilizing fat stores, regulating fat metabolism, and achieving fat homeostasis by inhibiting the hydroxylation of certain residues of HIFα, e.g., proline residues, asparagine residues, etc. In a preferred embodiment, the residues are proline residues. In specific embodiments, the residues can be the $P_{564}$ residue in HIF-1α or a homologous proline in another HIFα isoform, or the $P_{402}$ residue in HIF-1α or a homologous proline in another HIFα isoform, etc. In other embodiments, the present methods may encompass inhibiting hydroxylation of HIFα asparagine residues, e.g., the $N_{803}$ residue of HIF-1α or a homologous asparagine residue in another HIFα isoform.

Compounds

In one aspect, the present invention provides methods for decreasing adipose, tissue formation and fat deposition, mobilizing fat stores, regulating fat metabolism, and achieving fat homeostasis by administering a compound of the invention to a subject. A compound of the invention is any compound that inhibits or otherwise modulates the activity of a 2-oxoglutarate dioxygenase enzyme. 2-oxoglutarate dioxygenase enzymes include, but are not limited to, hydroxylase enzymes. Hydroxylase enzymes hydroxylate target substrate residues and include, for example, prolyl, lysyl, asparaginyl (asparagyl, aspartyl)hydroxylases, etc. Hydroxylases are sometimes described by target substrate, e.g., HIF hydroxylases, procollagen hydroxylases, etc., and/or by targeted residues within the substrate, e.g., prolyl hydroxylases, lysyl hydroxylases, etc., or by both substrate and residue, e.g., HIF prolyl hydroxylases, procollagen prolyl hydroxylases, etc. Representative 2-oxoglutarate dioxygenase enzymes include, but are not limited to, HIF hydroxylases, including HIF prolyl hydroxylases, e.g., EGLN1, EGLN2, and EGLN3, HIF asparaginyl hydroxylases, e.g., factor inhibiting HIF (FIH), etc.; procollagen hydroxylases, e.g., procollagen lysyl hydroxylases, procollagen prolyl hydroxylases, e.g., procollagen prolyl 3-hydroxylase, procollagen prolyl 4-hydroxylase α(I) and α(II), etc.; thymine 7-hydroxylase; aspartyl (asparaginyl) β-hydroxylase; ε-N-trimethyllysine hydroxylase; γ-butyrobetaine hydroxylase, etc. Although enzymatic activity can include any activity associated with any 2-oxoglutarate dioxygenase, the hydroxylation of amino acid residues within a substrate is specifically contemplated. Although hydroxylation of proline and/or asparagine residues within a substrate is specifically included, hydroxylation of other amino acids is also contemplated.

In certain embodiments, a compound of the invention is a compound that inhibits hydroxylase activity. In preferred embodiments, a compound of the invention is a compound that inhibits HIF hydroxylase activity. In various embodiments, the activity is due to a HIF prolyl hydroyxase, such as, for example, EGLN1, EGLN2, or EGLN3, etc. In other embodiments, the activity is due to a HIF asparaginyl hydroxylase including, but not limited to, FIH.

In one aspect, a compound of the invention that shows inhibitory activity toward one or more 2-oxoglutarate dioxygenase enzyme may also show inhibitory activity toward one or more additional 2-oxoglutarate dioxygenase enzymes, e.g., a compound that inhibits the activity of a HIF hydroxylase may additionally inhibit the activity of a collagen prolyl hydroxylase, a compound that inhibits the activity of a HIF prolyl hydroylxase may additionally inhibit the activity of a HIF asparaginyl hydroylxase, etc.

In one aspect, the present invention provides methods for decreasing adipose, tissue formation and fat deposition, mobilizing fat stores, regulating fat metabolism, and achieving fat homeostasis by administering a compound of the invention to a subject. A compound of the invention can be, e.g., a small molecule compound that inhibits HIF hydroxylase activity. In a preferred embodiment, a compound of the invention is a compound that inhibits HIF prolyl hydroxylase activity. The inhibition can be direct or indirect, can be competitive or non-competitive, etc. Exemplary compounds and methods for identifying additional compounds of the present invention are provided, infra.

In one aspect, the present invention provides methods for decreasing adipose tissue formation and fat deposition, mobilizing fat stores, modulating fat regulation, and achieving fat homeostasis by administering a compound of the invention to a subject. The compounds of the present invention can be used to regulate body weight or to facilitate a reduction in body weight, e.g., in overweight or obese subjects. Additionally, the compounds can be used to treat disorders or conditions associated with fat metabolism including, but not limited to, atherosclerosis, obesity, etc.

In one aspect, the present invention provides methods of using the compounds to prevent or treat a disorder, the method comprising administering an effective amount of the compound or a pharmaceutically acceptable salt or prodrug thereof either alone or in combination with a pharmaceutically acceptable excipient to a patient in need. In one embodiment, the compound can be administered based on pre-disposing conditions, e.g. difficulty controlling body weight or obesity.

The compounds can be administered in combination with various other therapeutic approaches. In one embodiment, the compound is administered with or in place of another therapeutic agent having the same or different mode of action, e.g., a glucocorticoid, exogenous insulin, e.g., human recombinant insulin, a PPARγ agonist, e.g., thiazolidinediones, or an appetite suppressant.

Expression of Fat Regulatory Factors

The methods of the present invention provide means for altering expression of regulatory factors involved in fat metabolism, e.g., fat transport, uptake, utilization, synthesis, processing, and storage throughout the body. In one aspect, the methods compensate for defects in the body's natural mechanisms for regulating such processes, e.g., due to altered production of and/or response to physiological factors such as leptin, plasminogen activator inhibitor (PAI)-1, insulin, etc. In another aspect, the methods modulate, e.g., increase or decrease, the level and/or activity of regulatory factors, e.g., transcriptional regulators, involved in fat transport, uptake, and utilization such as DEC1/Stra13, peroxisome proliferator-associated receptors (PPARs), etc.

Leptin is a key regulator of body weight, producing effects on both food intake and energy expenditure. Although adipocytes are the major source of leptin production, other tissues including placenta, skeletal muscle, stomach mucosa, and mammary epithelium also produce leptin. (See, e.g., Ahima and Flier (2000) Annu Rev Physiol 62:413-437; Fantuzzi and Faggioni (2000) J Leukocyte Biol 68:437-446.) Leptin-deficient mice (ob/ob) are extremely overweight due to chronic excessive food intake and administering exogenous leptin to ob/ob mice produces a dramatic reduction in food intake and weight loss. (Zhang et al. (1994) Nature 372:425-431; Pelleymounter et al. (1995) Science 269:540-543; Halaas et al. (1995) Science 269:543-546; and Campfield et al. (1995) Science 269:546-549.) Similarly, mice deficient in leptin receptor (db/db) are also overweight. Also, upregulation of PAI-1, a major stress induced gene with an established anti-obesity effect, would provide benefit in disorders associated with fat homeostasis such as obesity and diabetes.

As the methods and compounds of the present invention increased leptin expression, the methods and compounds are useful for regulating fat metabolism, energy utilization, and satiety. The methods would be especially useful to prevent weight gain in a subject. Further, the methods and compounds of the present invention increased plasminogen activator inhibitor (PAI)-1 expression. Thus, the methods are also useful for regulating weight in a subject, particularly providing benefit in disorders associated with fat homeostasis such as obesity and diabetes.

A family of ligand-activated transcription factors called PPARs regulates cellular response to fatty acids and triglycerides. DEC1/Stra13, a member of the *Drosophila* hairy/Enhancer of split transcription repressor family, is known to repress expression of, e.g., PPAR-γ2, a transcription factor necessary for adipocyte differentiation and associated with obesity and type 2 diabetes. (See, e.g., Yun et al. (2002) Dev Cell 2:331-341; Giusti et al. (2003) Diabetes 52:1673-1676; and Muller et al. (2003) Diabetes 52:1864-1871.) Thus, modulation of DEC1/Stra13 and/or PPARs, e.g., PPAR-γ2, would provide additional benefit by regulating expression of adipogenic factors, including factors involved in fat uptake and cellular processing.

As the methods and compounds of the present invention modulated levels of factors including DEC1/Stra13 and peroxisome proliferator-associated receptors (PPARs) involved in cellular response to fat levels, the methods and compounds are useful for regulating expression of genes involved in cellular response to fat, particularly in cellular uptake and processing of fatty acids and triglycerides.

The invention provides methods for coordinated regulation of genes whose products are involved in fat metabolism. Such genes include, but are not limited to, genes relating to uptake and transport of dietary fat, de novo fat synthesis and transport, and fat processing (breakdown), utilization, etc., including, e.g., glycerol 3-phosphate acyl transferase (GPAT), long chain fatty acyl CoA synthase, carnitine acetyl transferase, etc. Therapeutic upregulation of fat metabolism enzymes and satiety factors will effectively reduce fat storage, decrease body weight and, thereby, produce a beneficial effect in patients with metabolic disorders, e.g., obesity. In yet another embodiment, the methods of the invention provide coordinated regulation of genes whose products are involved in fat transport. Such genes include, but are not limited to, apolipoprotein (Apo) A-IV.

For example, CoA thioesterases (CTEs) and carnitine acetyl transferase (CAT) regulate acyl-CoA levels in cells. (van der Liej et al. (2000) Mol Genet Metab 71:139-153; Huhtinen et al. (2002) J Biol Chem 277:3424-3432). Long-chain acyl-CoA esters are used in triglyceride synthesis and 13-oxidation. Additionally, long-chain acyl-CoA esters may stimulate peroxisome proliferator activated receptor (PPAR)-α activity, thereby influencing gene transcription. ApoA-IV is a component of chylomicrons and high density lipoprotein (HDL) particles, and when overexpressed promotes efflux of cholesterol from cholesterol-laden cells (Cohen et al. (1997) J Clin Invest 99:1906-1916.) Overexpression of ApoA-IV also protects against atherosclerosis. (Duverger et al. (1996) Science 273:966-968. Also see, e.g., Ordovas et al. (1989) J Biol Chem 264:16339-16342; Otha et al. (1985) J Clin Invest 76:1252-1260; and Verges (1995) Diabetes Metab 21:99-105.) Thus, increased expression of genes involved in fat regulation, e.g., CTE-1 and ApoA-IV, as presently demonstrated using the compounds and methods of the invention, may provide both direct and indirect regulation of fat metabolism and transport.

Therefore, the methods and compounds of the present invention modulate levels of factors involved in fat metabolism, and are useful for regulating fat metabolism in a subject. In one aspect, the methods of the invention regulate expression of proteins involved in triglyceride production and/or utilization. Therapeutic upregulation of fat metabolism enzymes will effectively reduce fat storage, decrease body weight and, thereby, produce a beneficial effect in patients with metabolic disorders, e.g., obesity. Further, the methods and compounds of the present invention modulated levels of factors, such as apolipoproteins, involved in fat transport. Therefore, the methods of the invention can be used to regulate processing and transport of fatty acids and triglycerides between cells including muscle, liver, heart, and adipose. Altering transport processes further directs use of fat, favoring fat utilization over storage.

The invention specifically contemplates selectively designing prodrug compounds such that they are activated upon uptake by specific organs. For example, as the liver produces many of the proteins involved in fat homeostasis, the invention contemplates selectively targeting the liver in the present methods. Selective upregulation of genes, e.g., ApoA-IV, in the liver can be achieved using compounds that are converted from an inactive to an active form by liver specific enzymes. For example, a carboxylic acid on an active compound can be replaced with a corresponding alcohol. The activity of alcohol dehydrogenase (ADH) in the liver would convert such a compound into active form. As other organs lack ADH activity, the compound would be selectively activated only in the liver. Similarly, compounds used in the method of the invention may be targeted to other organs, e.g., adipose tissue, kidney, skeletal muscle, heart, etc.

Metabolic Shift in Energy Production

The body obtains energy from fatty acid and carbohydrate utilization. Both glucose and fatty acids can be used for energy immediately upon uptake, but amounts consumed in excess of current energy demand are stored for later use. Since only a limited amount of glucose can be stored as glycogen, most of the glucose consumed is converted to fatty acids and stored in adipose tissue. Thus, adipose tissue contains the major energy reserve for an organism. Further, not only does adipose tissue serve as a source of energy stores, but it also serves multiple endocrine and thermoregulatory functions, and is involved in the regulation of glucose metabolism.

As discussed above, the liver is also involved in fat and glucose metabolism, performing a critical and central role in maintaining proper blood levels of these vital nutrients. Although glucose is the primary fuel of neurons and red blood cells, most other tissues rely on fatty acids for their basic energy needs. Upon reduction of normal blood glucose levels, the liver breaks down glycogen and adipose tissue breaks down triglycerides to supply glucose and fatty acids, respectively, to the blood. Insulin is an important regulator of this metabolic equilibrium, stimulating glucose uptake in fat and muscle, glycogen synthesis, and lipogenesis. Low insulin levels decrease glucose uptake in insulin-sensitive tissues, promote gluconeogenesis and glycogenolysis in the liver, decrease glycogen synthesis, and promote mobilization of stored fatty acids from adipose.

It can be desirable to shift the body's energy production to include pathways requiring fat as an energy source. Under conditions of low blood glucose levels or impaired glucose regulation, e.g., diabetes, the use of fat as an energy source can provide an alternative fuel for most tissues, thus making potentially limiting quantities of glucose available to organs that require it. In addition, increased utilization of fat as an energy source can lead to a reduction in stored fat, thereby inducing weight loss, e.g., in an obese individual, or prevent development and progression of obesity associated with conditions such as diabetes. The present invention provides methods and compounds for enhancing fat utilization by regulating fat metabolism, e.g., by enhanced expression of fat regulatory factors, etc., reducing fat stores, and preventing additional deposition of fat (see, e.g., Examples 3, 5, and 6, infra). Therefore, in one aspect, the present methods and compounds provide for a metabolic shift enhancing the body's utilization of fat as an energy source; i.e., a metabolic shift towards utilization of fat as an energy source; i.e., production of energy from fat.

Regulation of lipogenic enzymes (see, e.g., Example 3) occurs in coordination with the regulation of glucose transport, glycolysis, and gluconeogenesis for the reasons discussed above. For example, feeding previously fasted animals high-carbohydrate, low-fat diets results in an increase in enzymes involved in fatty acid and triacylglycerol biosynthesis, and glycolysis, as well as an increase in glucose uptake via glucose transporters. (See, e.g., Sul and Wang (1998) Annu Rev Nutr 18:331-351.) Thus, in particular embodiments, the methods of the invention provide coordinated regulation of genes whose products are involved in glucose uptake and utilization. Such genes include, but are not limited to, glycolytic enzymes including phosphofructokinases, enolase, lactate dehydrogenase, aldolase, and hexokinases; and glucose transporters (GluTs). An increase in glycolysis leads to enhanced uptake and utilization of glucose, which can be associated with a decrease in blood glucose levels. As the methods of the invention can simultaneously be applied to enhance expression of fat regulatory factors, and increase the body's ability to use fat as an energy source, the present invention thus provides a protective mechanism for simultaneously achieving and/or preserving glucose and fat homeostasis. The present methods and compounds are thus particularly applicable to treatment or prevention of conditions such as, e.g., diabetes, in which altered or impaired glucose and fat regulation—such as evidenced by elevated glucose levels and obesity or a tendency to obesity—can be causally related.

Additionally, the shift to increased glycolysis, an anaerobic process, and increased fatty acid utilization could effectively reduce net oxygen consumption. (See, e.g., Example 12.) The metabolic shift in energy utilization and accompanying weight reduction are consistent with reports that hypoxia associated with high altitude induces weight loss, specifically manifested as a reduction in body fat. (See, e.g., Fushiki et al., supra; Gunga et al., supra; and Tschop and Morrison, supra.) This approach can be used, e.g., to preserve or increase the body's ability to generate energy. This can be desirable, e.g., under low oxygen conditions, or under conditions in which it is desirable to enhance the body's ability to sustain and/or to increase physical exertion, etc. Therefore, in one aspect, the present invention provides methods and compounds for inducing a metabolic shift in oxygen consumption, i.e., producing a dose-dependent reduction in oxygen consumption in cells without any affect on cell viability. The present invention contemplates that the shift to anaerobic energy production, a less-efficient process than aerobic respiration, will increase the body's need to turn to fat as an energy source, thus effecting an additional metabolic shift, e.g., towards fat as a primary energy source.

In one embodiment, the present invention contemplates a method for inducing a decrease in aerobic metabolism and a concomitant increase in anaerobic metabolism in a subject, the method comprising: (a) altering expression of a glycolytic factor; and (b) altering in coordinated fashion a fat regulatory factor. In various embodiments, the glycolytic factor is selected from the group consisting of PFK-P, PFK-L, enolase-1, GluT-1, lactate dehydrogenase, aldolase-1, hexokinase-1, IGFBP-1, and IGF, and the fat regulatory factor is selected from the group consisting of leptin, apolipoprotein A-IV, cytosolic acyl CoA thioesterase-1, insulin-like growth factor binding protein (IGFBP)-1, carnitine acetyl transferase, PAI-1, DEC1/Stra13, and PPAR-γ.

The invention specifically contemplates a coordinated therapeutic approach through which the administration of one compound of the invention simultaneously achieves coordinate upregulation of at least one fat regulatory factor and at least one glucose regulatory factor.

While the present invention is by no means limited to the exemplary process described below, it is contemplated that the increased utilization of fat as an energy source, as evidenced by, e.g., reduction in body fat (see, e.g., Example 5 and 6, etc.) and short-term increase in triglycerides (see, e.g., Example 13), effectively decreases net energy efficiency, causing the subject to burn more calories to produce energy, and thus inducing weight loss. The long-term decrease in triglyceride levels (see, e.g., Example 8) is supportive of this theory, demonstrating that the ultimate effect of the present methods in regulating fat metabolic processes is to drive the body to achieve and to maintain fat homeostasis.

Therefore, in one aspect, the present invention provides a method of decreasing energy efficiency in a subject, and thereby inducing weight loss, the method comprising stabilizing HIFα in a subject.

Therapeutic Methods

The present invention provides methods and compounds for treating metabolic disorders associated with fat metabolism and homeostasis. Further, the invention provides methods for treating a patient having a high likelihood of developing a metabolic disorder, e.g., individuals at high risk for atherosclerosis, diabetes, etc., using the compounds described herein. Risk factors for atherosclerosis and diabetes include, e.g., hyperlipidemia and abdominal obesity.

The metabolic state of a subject is physiologically controlled by factors that respond to plasma levels of key metabolites and alter expression of a repertoire of genes that appropriately manage nutrient utilization and storage. For example, metabolic homeostasis of adipose tissue requires a balance between glucose and triglyceride uptake and storage and fatty acid release. The present invention provides methods and compounds for regulating the metabolic state of a subject, wherein the subject may be a cell grown in culture or an animal, preferably wherein the animal is a mammal, and more preferably wherein the mammal is a human.

Altered or impaired fat metabolism, or an excess of or lack in fat stores, can lead to, in the case of excess fat stores, obesity, including abdominal obesity, an aggravating factor for diabetes; in the case of depletion or low fat stores, impaired immune function; and other metabolic abnormalities.

Obesity, especially abdominal or central obesity, is very common in patients with Type 2 diabetes. Adipocytes are a major target organ of insulin; adipocytes also secrete a number of biologic products such as leptin, tumor necrosis factor-α, and free fatty acids, which modulate secretion and action of insulin. Thus, excess adipose tissue may contribute to insulin resistance. For example, loss-of-function mutations in the gene that encodes leptin are associated with a predisposition to diabetes in rodents. (Chen et al. (1996) Cell 84:491-495.)

Several other proteins associated with fat regulation appear to provide benefits in diabetes and vascular disease as well. For example, ApoA-IV has antiatherogenic properties; and mice lacking PAI-1 are less able to control body weight, gaining weight faster on a high fat diet than wild type mice. (See, e.g., Cohen et al. (1997) J Clin Invest 99:1906-1916; Verges (1995) Diabetes Metab 21:99-105; Ostos et al. (2000) Atherosclerosis 153:209-217; and Morange et al. (2000) Arterioscler Thromb Vasc Biol 20:1150-1154.) In addition, PAI-1 expression is enhanced by the pro-cachectic cytokine TNF-α and by antidiabetic compounds of the thiazolidinedione type. (Cigolini et al. (1999) Atherosclerosis 143:81-90; and Ihara et al. (2001) FASEB J 15:1233-1235.) Additionally, expression of proteins such as insulin-like growth factor binding protein (IGFBP)-1 results in enhanced insulin sensitivity and contributes to reduction of body fat mass.

Obesity can also be associated with increased activity of the sympathetic nervous system, elevated plasma levels of the vasoconstrictor endothelin-1, and decreased insulin-induced endothelium-dependent vasodilation. Furthermore, adipocytes can secrete vasogenic peptides, such as angiotensinogen. Type 2 diabetes, visceral obesity, arterial hypertension, and lipid disorders may belong to a syndrome caused by decreased insulin sensitivity with compensatory hyperinsulinemia, which pose significant coronary risk. (Muller-Wieland et al. (1998) Basic Res Cardiol 93:131-134.)

Accordingly, the present methods can be applied to pharmacologically stabilize HIFα and thereby produce the appetite suppression and subsequent weight loss associated with hypoxic environmental stimuli. The present invention demonstrates that the methods described herein result in a selective reduction of body fat, macroscopically observed as disappearance of abdominal fat pads and increased relative organ weight, in animal models. These effects were observed in genetically normal animals, demonstrating that the methods are able to appropriately upregulate all of the factors that are necessary to effectively reduce body fat mass.

As the methods of the invention effectively modulate numerous aspects of fat regulation, including fat transport, uptake, processing, utilization, and storage, the methods are useful in treating or preventing disorders associated with fat regulation. Such disorders include, but are not limited to, obesity, atherosclerosis, etc. Since excess fat and lipids are known to contribute to the risks associated with development of diabetes, treatment with the current methods may have beneficial effects on reducing the likelihood, frequency, or severity of diabetes. Furthermore, high serum levels of free fatty acids or lipids are known to increase insulin resistance, which further exacerbates the pathophysiology of diabetes.

The compounds and methods of the present invention can be used for regulating body weight, inducing loss or reduction in body mass without concomitant loss of muscle mass. Specifically, the methods of the present invention can be used in reducing visceral fat levels and deposition. Further, the methods of the invention potentially reduce adipogenesis and regulate fat storage, thereby effectively controlling weight gain. Such methods are useful in the treatment of disorders in fat metabolism or in facilitating maintenance of appropriate body weight. Additionally, the methods and compounds of the invention are effective at reducing weight gain even during excessive caloric intake. Thus, pharmacologic regulation of HIF stabilization provides a novel therapeutic approach for treating or preventing the complications, diseases, and pathology associated with fat regulation, e.g., obesity. By increasing anti-lipogenic factors, such as leptin, PAI-1, ApoA-IV, and IGFBP, HIF stabilization provides therapeutic benefits to obesity and associated complications.

Pharmaceutical Formulations and Routes of Administration

The compositions of the present invention can be delivered directly or in pharmaceutical compositions containing excipients, as is well known in the art. Present methods of treatment can comprise administration of an effective amount of a compound of the present invention to a subject having or at risk for having a metabolic disorder; particularly a disorder associated with fat regulation, e.g., atherosclerosis, obesity, diabetes, etc. In a preferred embodiment, the subject is a mammalian subject, and in a most preferred embodiment, the subject is a human subject.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, Ed. (2000) *Remington's Pharmaceutical Sciences*, supra; and Hardman, Limbird, and Gilman, Eds. (2001) *The Pharmacological Basis of Therapeutics*, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., *Inactive Ingredient Guide* (1996); Ash and Ash, Eds. (2002) *Handbook of Pharmaceutical Additives*, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derided from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician, e.g., regulation of fat metabolism, reduction of body fat, regulation of body weight, treatment or prevention of a disorder, e.g., obesity, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, e.g., regulation of fat metabolism, reduction in body weight, fat stores, etc.; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Compounds and Screening Methods Therefor

A compound of the invention is a compound that inhibits hydroxylase activity, specifically wherein the hydroxylase activity is the activity of a 2-oxoglutarate dioxygenase enzyme. More preferably, the hydroxylase activity is the activity of a HIF hydroxylase enzyme. Most preferably, the hydroxylase activity is the activity of a HIF prolyl hydroxylase enzyme A method of the invention is a method that relies on the stabilization of HIFα to achieve a particular result in a subject. Preferably, the methods of the present invention are accomplished through administration of a compound to stabilize HIFα and achieve a particular result in that subject. Most preferably, the methods are accomplished by administration of a compound of the invention.

The compounds of the present invention are exemplary for use in the present methods, which relate to stabilization of HIFα. In particular, the present invention provides compounds, and methods of screening for and identifying additional compounds that inhibit HIF hydroxylase activity and/or HIFα hydroxylation, stabilize HIFα, etc. Compounds of the invention include compounds that inhibit hydroxylase activity, preferably wherein the hydroxylase activity is the activity of a 2-oxoglutarate dioxygenase enzyme, and more preferably wherein the hydroxylase activity is the activity of a HIF hydroxylase. The HIF hydroxylase may hydroxylate any amino acid, including, e.g., a proline or asparagine residue, etc., in a HIF protein, preferably in a HIFα subunit. In an especially preferred embodiment, the hydroxylase activity is the activity of a HIF prolyl hydroxylase and/or a HIF asparaginyl hydroxylase.

Inhibitors of 2-oxoglutarate dioxygenase activity are known in the art. For example, several small molecule inhibitors of procollagen prolyl 4-hydroxylase have been identified. (See, e.g., Majamaa et al. (1984) Eur J Biochem 138:239-245; Majamaa et al. (1985) Biochem J 229:127-133; Kivirikko and Myllyharju (1998) Matrix Biol 16:357-368; Bickel et al. (1998) Hepatology 28:404-411; Friedman et al. (2000) Proc Natl Acad Sci USA 97:4736-4741; and Franklin et al. (2001) Biochem J 353:333-338; all incorporated by reference herein in their entirety.) Small molecule inhibitors of HIF hydroxylases have also been identified. (See, e.g., International Publication Nos. WO 02/074981, WO 03/049686, and WO 03/080566, all incorporated herein by reference in their entirety.) The present invention specifically contemplates the use of these and other compounds that can be identified using methods known in the art.

All of the enzymes in the 2-oxoglutarate dioxygenase family require oxygen, $Fe^{2+}$, 2-oxoglutarate, and ascorbic acid for their hydroxylase activity. (See, e.g., Majamaa et al. (1985) Biochem J 229:127-133; Myllyharju and Kivirikko (1997) EMBO J 16:1173-1180; Thornburg et al. (1993) 32:14023-14033; and Jia et al. (1994) Proc Natl Acad Sci USA 91:7227-7231.) Therefore, compounds of the invention include, but are not limited to, iron chelators, 2-oxoglutarate mimetics, and modified amino acid, e.g., proline or asparagine, analogs.

In particular embodiments, the present invention provides for use of structural mimetics of 2-oxoglutarate. Such compounds may inhibit the target 2-oxoglutarate dioxygenase enzyme competitively with respect to 2-oxoglutarate and noncompetitively with respect to iron. (Majamaa et al. (1984) supra; and Majamaa et al. (1985) supra.) Specifically contemplated are compounds described, e.g., in Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19:812-815; Franklin et al. (2001) Biochem J 353:333-338; and International Publication No. WO 03/049686, all incorporated by reference herein in their entirety.

Exemplary compounds include phenanthrolines including, but not limited to, those described in U.S. Pat. Nos. 5,916,898 and 6,200,974, and International Publication No. WO 99/21860; heterocyclic carbonyl glycines including, but not limited to, substituted quinoline-2-carboxamides and esters thereof as described, e.g., in U.S. Pat. Nos. 5,719,164 and 5,726,305; substituted isoquinoline-3-carboxamides and esters thereof as described, e.g., in U.S. Pat. No. 6,093,730; 3-methoxy pyridine carbonyl glycines and esters thereof as described, e.g., in European Patent No. EP 0 650 961 and U.S. Pat. No. 5,658,933; 3-hydroxypyridine carbonyl glycines and esters thereof as described, e.g., in U.S. Pat. Nos. 5,620,995 and 6,020,350; 5-sulfonamidocarbonyl pyridine carboxylates and esters thereof as described, e.g., in U.S. Pat. Nos. 5,607,954, 5,610,172, and 5,620,996. All compounds listed in these patents, in particular, those compounds listed in the compound claims and the final products of the working examples, are hereby incorporated into the present application by reference herein.

Therefore, preferred compounds of the present invention include, e.g., heterocyclic carboxamides. Specifically preferred heterocyclic carboxamides include, e.g., isoquinolines, quinolines, pyridines, cinnolines, carbolines, etc. Additional structural classes of preferred compounds include anthraquinones, azafluorenes, azaphenanthrolines, benzimidazoles, benzofurans, benzopyrans, benzothiophenes, catechols, chromanones, α-diketones, furans, N-hydroxyamides, N-hydroxyureas, imidazoles, indazoles, indoles, isothiadiazoles, isothiazoles, isoxadiazoles, isoxazoles, α-keto acids, α-keto amides, α-keto esters, α-keto imines, oxadiazoles, oxalyl amides, oxazoles, oxazolines, purines, pyrans, ppyrazines, pyrazoles, pyrazolines, pyridazines, pyridines, quinazolines, phenanthrolines, tetrazoles, thiadiazoles, thiazoles, thiazolines, thiophenes, and triazoles.

The following exemplary compounds are used in the present examples to demonstrate the methods of the invention described herein: [(7-Chloro-3-hydroxy-quinoline-2-carbonyl)-amino]-acetic acid (compound A), [(1-Chloro-4-hydroxy-isoquinoline-3-carbonyl)-amino]-acetic acid (compound B), [(4-Hydroxy-7-phenoxy-isoquinoline-3-carbonyl)-amino]-acetic acid (compound C), 4-Oxo-1,4-dihydro-[1,10]phenanthroline-3-carboxylic acid (compound D), [(1-Chloro-4-hydroxy-7-methoxy-isoquinoline-3-carbonyl)-amino]-acetic acid (compound E), [(3-Hydroxy-6-isopropoxy-quinoline-2-carbonyl)-amino]-acetic acid (compound F), [(3-Hydroxy-pyridine-2-carbonyl)-amino]-acetic acid (compound G), and [(7-Benzyloxy-1-chloro-4-hydroxy-isoquinoline-3-carbonyl)-amino]-acetic acid methyl ester (compound H).

Various assays and screening techniques, including those described below, can be used to identify compounds of the present invention, i.e., compounds that inhibit hydroxylase activity. These compounds are suitable for use in the present methods. Additional compounds suitable for use in the present methods, i.e., compounds that stabilize HIFα, can be identified by one of skill in the art using available assay and screening methodology.

Assays will typically provide for detectable signals associated with the consumption of a reaction substrate or production of a reaction product. Detection can involve, for example, fluorophores, radioactive isotopes, enzyme conjugates, and other detectable labels well known in the art. The results may be qualitative or quantitative. Isolation of the reaction product may be facilitated by a label, such as biotin or a histidine tag that allows purification from other reaction components via precipitation or affinity chromatography.

Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof. (See, e.g., Palmerini et al. (1985) J Chromatogr 339:285-292.) A reduction in hydroxylated residue, e.g., proline or asparagine, in the presence of a compound is indicative of a compound that inhibits hydroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990; Anal Biochem 184: 291-297) describe an exemplary procedure that measures production of succinate from 2-oxoglutarate.

Procedures such as those described above can be used to identify compounds that modulate HIF hydroxylase activity. An exemplary procedure is described in Example 8 (infra). Target protein may include HIFα or a fragment thereof, e.g., HIF(556-575); for example, an exemplary substrate for use in the assay described in Example 9 is DLDLEMLAPYIPMDDDFQL (SEQ ID NO:1). Enzyme may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity are described in Ivan et al. (2001, Science 292:464-468; and 2002, Proc Natl Acad Sci USA 99:13459-13464) and Hirsila et al. (2003, J Biol Chem 278:30772-30780); additional methods are described in International Publication No. WO 03/049686. Measuring and comparing enzyme activity in the absence and presence of the compound will identify compounds that inhibit hydroxylation of HIFα.

Assays for HIFα stabilization and/or HIF activation may involve direct measurement of HIFα in a sample (see, e.g., Example 8, infra), indirect measurement of HIFα, e.g., by measuring a decrease in HIFα associated with the von Hippel Lindau protein (see, e.g., International Publication No. WO 00/69908), or activation of HIF responsive target genes or reporter constructs (see, e.g., U.S. Pat. No. 5,942,434). Measuring and comparing levels of HIF and/or HIF-responsive target proteins in the absence and presence of the compound will identify compounds that stabilize HIFα and/or activate HIF.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Test Materials

In general, compounds of the present invention were synthesized using standard chemical methods known to those of skill in the art. Compounds were analyzed for purity by high pressure liquid chromatography and stored at room temperature protected from light. During formulation for various uses, compounds were micronized in suspension at either 500 rpm for 25 minutes or 750 rpm for 10 min using a PULVERISETTE 7 planetary micro mill (Fritsch GMBH, Germany) to facilitate uniform particle size.

Suspensions of micronized compound Cor oral gavage were prepared immediately before use. Compound was suspended in aqueous solution containing 0.5% sodium carboxymethylcellulose (CMC; Spectrum Chemical, Gardena Calif.), 0.1% polysorbate 80 (Mallinckrodt Baker, Inc., Phillipsburg N.J.) and stirred constantly using a magnetic stirrer or rotary shaker during dose administration. The concentration of the suspensions was calculated to achieve the intended dose level in a given volume. In alternative procedures, compound was weighed and placed in appropriately sized gelatin capsules for oral administration, wherein control animals received empty capsules of the same size; or compound was dissolved in a 100 mM histidine (Mallinckrodt Baker) solution and provided ad libitum in place of water.

For administration by injection, compound was initially mixed with an equimolar amount of sodium hydroxide, in either an aqueous solution of 10% glucose (Spectrum) or 25 mM histidine combined with sodium chloride at isotonicity (Mallinckrodt Baker).

Example 2

Increased In Vitro Expression of Leptin in Select Cell Types

The effect of the methods and compounds of the invention on fat regulation and, in particular, on expression of factors associated with fat metabolism and satiety was examined as follows. Human HeLa (cervical epithelial carcinoma), 293A (adenovirus-transformed fetal kidney epithelium; Qbiogene, Carlsbad Calif.), Hep3B (hepatocellular carcinoma), HFF (foreskin fibroblast), HMEC-1 (microvascular endothelial), HUVEC (umbilical vein endothelial), and adipocyte cells were separately seeded into 24 well culture dishes at 100,000 cells per well and cultured for 1 day at 37° C., 20% $O_2$, 5% $CO_2$ in the following media: HeLa, 293A and Hep3B in DMEM containing 1% FBS and 1% penicillin-streptomycin; HMEC-1 and HUVEC in Endothelial Growth Media (EGM-2; Cambrex, Walkersville Md.), HFF in DMEM containing 10% FBS and 1% penicillin-streptomycin, and adipocytes in Adipocyte media (Zen-Bio, Research Triangle Park N.C.). Media was then replaced with fresh medium as above except the serum level in the HeLa, 293A, Hep3B, and HFF cultures was reduced to 0.5% FBS. Vehicle control (0.5% DMSO) or compound B was added and the cells were incubated for an additional 3 days. Cell-free supernatants were then harvested and leptin levels were quantitated using a QUANTIKINE immunoassay (R&D Systems, Inc., Minneapolis Minn.) according to the manufacturer's instructions.

As shown in FIG. 1A, increased expression of leptin was observed in adipocytes, but not in other cell types, following treatment with a compound of the present invention.

In a separate experiment, preadipocytes were plated in 24 well plates at 45,000 cells per well and cultured for 3 days in preadipocyte media (Zen-Bio). The media was then changed to differentiation media (Zen-Bio) and cells were treated with either vehicle control (0.5% DMSO) or compound B at 25 or 50 μM for up to 12 days. Half of the culture media was exchanged every 3 days and cell-free culture supernatants were generated and analyzed for levels of leptin secretion using a QUANTIKINE immunoassay (R&D Systems) according to the manufacturer's instructions.

As shown in FIG. 1B, treatment of preadipocytes with compound B produced a dose-dependent increase in leptin secretion as compared to cells treated with vehicle control, and the levels of leptin continued to increase over the entire 12 day period.

In a similar experiment, adipocytes were seeded into 24 well plates at 100,000 cells per well in adipocyte media (Zen-Bio) and treated with either vehicle control, compound A, compound E, or compound F at 25 μM, or compound B at 25 or 50 μM. Half of the culture media was exchanged every 3 days and cell-free culture supernatants were generated and analyzed for levels of leptin secretion using a QUANTIKINE immunoassay (R&D Systems) according to the manufacturer's instructions.

As shown in FIG. 1C, treatment of adipocytes with compounds of the invention produced an increase in leptin secretion as compared to cells treated with vehicle control, and the levels of leptin continued to increase over the entire 12 day period.

Leptin is a regulatory factor involved in fat regulation and metabolism—transport, storage, processing, utilization, etc.—and appetite suppression, etc. The ability of the present compounds and methods to regulate expression of leptin suggests the use of the compounds and methods to regulate fat metabolism, and, in application to certain subjects, to reduce or prevent weight gain, or even induce weight loss.

Example 3

Increased Expression of Factors Involved in Fat Regulation

The ability of the present compounds and methods to regulate fat metabolism, in particular, to increase expression of factors involved in fat transport, utilization, and storage, was analyzed as follows. To determine gene induction patterns over time, twenty four Swiss Webster male mice (30-32 g) were obtained from Simonsen, Inc. and treated by oral gavage with a 4 ml/kg volume of either 0.5% carboxymethyl cellulose (CMC; Sigma-Aldrich, St. Louis Mo.) (0 mg/kg) or 1.25% compound B (25 mg/ml in 0.5% CMC) (100 mg/kg). At 4, 8, 16, 24, 48, or 72 hours after the final dose, animals were anesthetized with isoflurane. The mice were then sacrificed and tissue samples of kidney, liver, brain, lung, and heart were isolated and stored in RNALATER solution (Ambion) at −80° C.

RNA isolation was carried out using the following protocol. A 50 mg section of each organ was diced, 875 μl of RLT buffer (RNEASY kit; Qiagen Inc., Valencia Calif.) was added, and the pieces were homogenized for about 20 seconds using a rotor-stator POLYTRON homogenizer (Kinematica, Inc., Cincinnati Ohio). The homogenate was micro-centrifuged for 3 minutes to pellet insoluble material, the supernatant was transferred to a new tube and RNA was isolated using an RNEASY kit (Qiagen) according to the manufacturer's instructions. The RNA was eluted into 80 μL of water and quantitated with RIBOGREEN reagent (Molecular Probes, Eugene Oreg.). Genomic DNA was then removed from the RNA using a DNA-FREE kit (Ambion Inc., Austin Tex.) according to the manufacturer's instructions. The absorbance at 260 and 280 nm was measured to determine RNA purity and concentration.

Alternatively, tissue samples were diced and homogenized in TRIZOL reagent (Invitrogen Life Technologies, Carlsbad Calif.) using a rotor-stator POLYTRON homogenizer (Kinematica). Homogenates were brought to room temperature, 0.2 volumes chloroform was added, and samples were mixed vigorously. Mixtures were incubated at room temperature for several minutes and then were centrifuged at 12,000×g for 15 min at 4° C. The aqueous phase was collected and 0.5 volumes of isopropanol were added. Samples were mixed, incubated at room temperature for 10 minutes, and centrifuged for 10 min at 12,000×g at 4° C. The supernatant was removed and the pellet was washed with 75% EtOH and centrifuged at 7,500 g for 5 min at 4° C. Genomic DNA was then removed from the RNA using a DNA-FREE kit (Ambion Inc., Austin Tex.) according to the manufacturer's instructions. The absorbance at 260 and 280 nm was measured to determine RNA purity and concentration.

RNA was precipitated in 0.3 M sodium acetate (pH 5.2), 50 ng/ml glycogen, and 2.5 volumes of ethanol for one hour at 20° C. Samples were centrifuged and pellets were washed with cold 80% ethanol, dried, and resuspended in water. Double stranded cDNA was synthesized using a T7-(dT)24 first strand primer (Affymetrix, Inc., Santa Clara Calif.) and the SUPERSCRIPT CHOICE system (Invitrogen) according to the manufacturer's instructions. The final cDNA was extracted with an equal volume of 25:24:1 phenol:chloroform:isoamyl alcohol using a PHASE LOCK GEL insert (Brinkman, Inc., Westbury N.Y.). The aqueous phase was collected and cDNA was precipitated using 0.5 volumes of 7.5 M ammonium acetate and 2.5 volumes of ethanol. Alternatively, cDNA was purified using the GENECHIP sample cleanup module (Affymetrix) according to the manufacturer's instructions.

Biotin-labeled cRNA was synthesized from the cDNA in an in vitro translation (IVT) reaction using a BIOARRAY HighYield RNA transcript labeling kit (Enzo Diagnostics, Inc., Farmingdale N.Y.) according to the manufacturer's instructions. Final labeled product was purified and fragmented using the GENECHIP sample cleanup module (Affymetrix) according to the manufacturer's instructions.

Hybridization cocktail was prepared by bringing 5 µg probe to 100 µl in 1× hybridization buffer (100 mM MES, 1 M [$Na^+$], 20 mM EDTA, 0.01% Tween 20), 100 µg/ml herring sperm DNA, 500 µg/ml acetylated BSA, 0.03 nM control oligo B2 (Affymetrix), and 1× GENECHIP eukaryotic hybridization control (Affymetrix). The cocktail was sequentially incubated at 99° C. for 5 minutes and 45° C. for 5 minutes, and then centrifuged for 5 minutes. The Murine genome U74AV2 array (MG-U74Av2; Affymetrix) was brought to room temperature and then pre-hybridized with 1× hybridization buffer at 45° C. for 10 minutes with rotation. The buffer was then replaced with 80 µl hybridization cocktail and the array was hybridized for 16 hours at 45° C. at 60 rpm with counter balance. Following hybridization, arrays were washed once with 6×SSPE, 0.1% Tween 20, and then washed and stained using R-phycoerythrin-conjugated streptavidin (Molecular Probes, Eugene Oreg.), biotinylated goat anti-streptavidin antibody (Vector Laboratories, Burlingame Calif.), and a GENECHIP Fluidics Station 400 instrument (Affymetrix) according to the manufacturer's micro__1v1 protocol (Affymetrix). Arrays were analyzed using a GENEARRAY scanner (Affymetrix) and Microarray Suite software (Affymetrix).

The Murine Genome U74AV2 array (Affymetrix) represents all sequences (~6,000) in Mouse UniGene database build 74 (National Center for Biotechnology Information, Bethesda Md.) that have been functionally characterized and approximately 6,000 unannotated expressed sequence tag (EST) clusters.

Figure 2B:
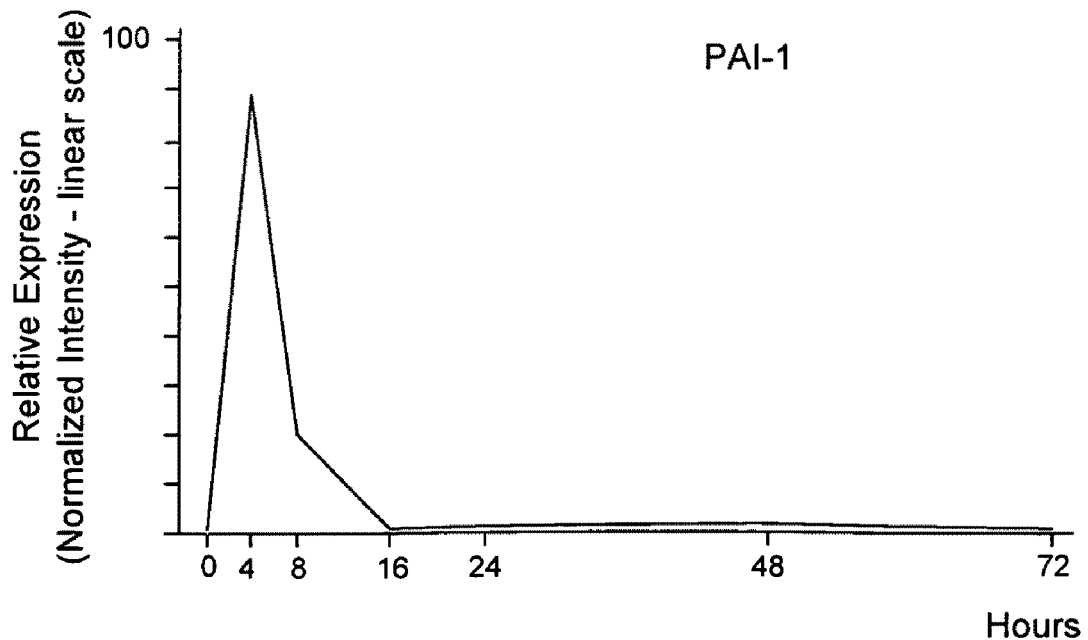

As shown in FIG. 2A, expression of genes encoding proteins involved in fat metabolism and transport was increased in liver in a coordinated fashion after treatment with a compound of the invention. Transcript patterns represented in FIG. 2A include (1) apolipoprotein A-IV, (2) cytosolic acyl CoA thioesterase-1, (3) insulin-like growth factor binding protein (IGFBP)-1, and (4) carnitine acetyl transferase. In the time course shown, mRNA levels for these proteins peaked early, then return to control levels after 24 h. FIG. 2B shows the specific expression time course for PAI-1, which showed a similar albeit earlier induction of expression following treatment with compounds of the present invention.

These data show that the present methods and compounds regulate fat metabolism by increasing expression in vivo of factors associated with fat storage, uptake, transport, synthesis, processing and utilization directly (e.g., ApoA-IV, carnitine thioesterases, carnitine acetyl transferases, PAIs, etc.) or indirectly (e.g. IGFBP-1, etc.). The present methods and compounds can be applied therapeutically to treat or prevent conditions associated with high cholesterol, e.g., atherosclerosis, etc., and impaired fat metabolism.

Example 4

Altered Expression of Regulatory Factors Involved in Adipocyte Differentiation

Figure 3A:
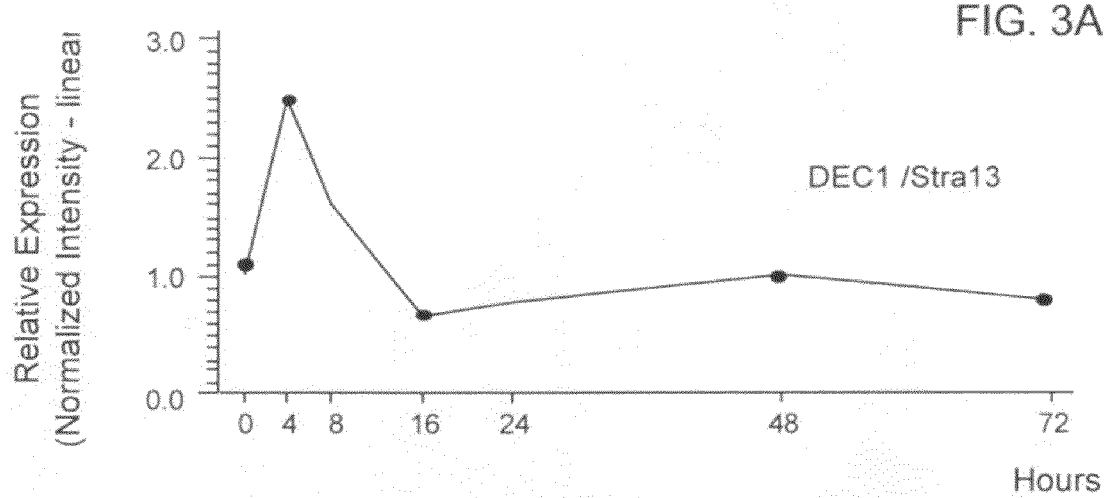
FIGS. 3A, 3B, and 3C show changes in expression of genes encoding factors involved in cellular response to fatty acids and triglycerides.

To further investigate the effect of the methods and compounds of the present invention on expression of genes associated with fat metabolism and adipogenesis, the experiments performed as described in Example 3 above were analyzed for specific adipogenic factors. As shown in FIG. 3A, expression of DEC1/Stra13 initially increased in liver of animals treated with compound B and then gradually returned to baseline by 72 hours after dosing. DEC1/Stra13 is known to repress expression of PPAR-γ2 nuclear hormone receptor, which is necessary for adipocyte differentiation. (See, e.g., Yun et al., supra; Giusti et al., supra; and Muller et al., supra.) Thus, as DEC1/Stra13 expression increases, the expression of PPAR-γ would be expected to decrease, reducing response of cells to fatty acids and, in particular, delaying adipocyte differentiation and generation of adipose tissue.

To further investigate the effect of the methods and compounds of the present invention on expression of adipogenic factors, twelve Swiss Webster male mice (30-32 g) obtained from Simonsen, Inc. were treated by oral gavage once per day for 4 days with 4 ml/kg volume of either 0.5% CMC (0 mg/kg/day), 25 mg/ml compound D in 0.5% CMC (100 mg/kg/day), or 7.5 mg/ml and 25 mg/ml of compound B in 0.5% CMC (30 and 100 mg/kg/day, respectively). Four hours after the final dose, animals were anesthetized, sacrificed, and approximately 150 mg of adipose, heart, kidney, liver, lung, and muscle were isolated and stored in RNALATER solution (Ambion) at −20° C. RNA isolation and gene expression analysis was performed as described in Example 3 above.

Figure 3B:
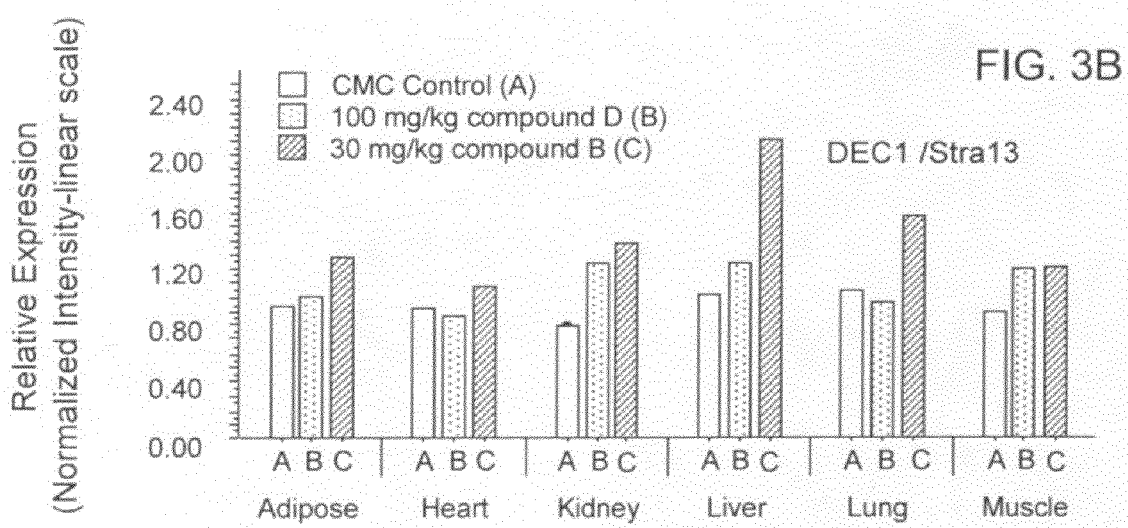
Figure 3C:
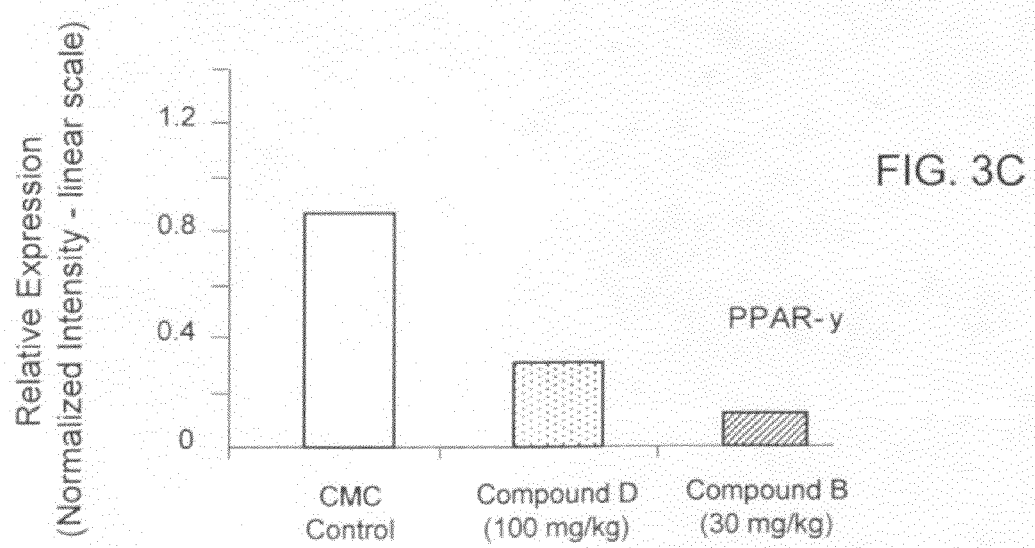

As shown in FIG. 3B, administration of either compound D or compound B led to increased DEC1/Stra13 expression in several tissues including adipose, kidney, liver, and muscle. Compound B also increased DEC1/Stra13 expression in lung and heart (FIG. 3B). Further, increased expression was still evident after 4 days of treatment. Further, administration of either compound D or compound B, as described above, led to decreased PPAR-γ expression, e.g., in cardiac tissue (FIG. 3C).

These data show that the present methods and compounds regulate fat metabolism by altering expression of factors involved in cellular response to fat, including triglyceride synthesis, utilization, transport, and storage. In particular, the present methods and compounds can be used to modulate adipocyte differentiation and reduce fat storage.

Example 5

In Vivo Regulation of Body Weight and Fat

The effect of the present compounds and methods on regulation of body weight and fat, e.g., through effect on fat stores, was examined as follows. Fifty male Sprague Dawley rats (6-7 weeks old) obtained from Simonsen, Inc. were dosed with 0.5% CMC (Sigma-Aldrich) or compound B at 20, 60, 100, or 200 mg/kg body weight by oral gavage once daily for 14 consecutive days. Animals were monitored for changes in body weight and signs of overt toxicity and mortality. On day 15, following an overnight fast with water available ad libitum, animals were anesthetized with isoflurane, the abdominal cavity was opened, and blood was collected from the inferior vena cava. One whole blood sample of approximately 1 ml was collected into tubes containing EDTA for hematological analysis, and a second sample of approximately 1 ml was collected into a tube with no anticoagulant for serum chemistry analysis. Blood sample analyses were performed by IDEXX (West Sacramento, Calif.). Following blood collection, the diaphragm was incised and the animals were sacrificed. Macroscopic observations were recorded for each animal and the liver, kidneys, heart, spleen, lungs, stomach, small intestines, and large intestines were collected for biochemical and/or histological assessment.

Figure 4A:
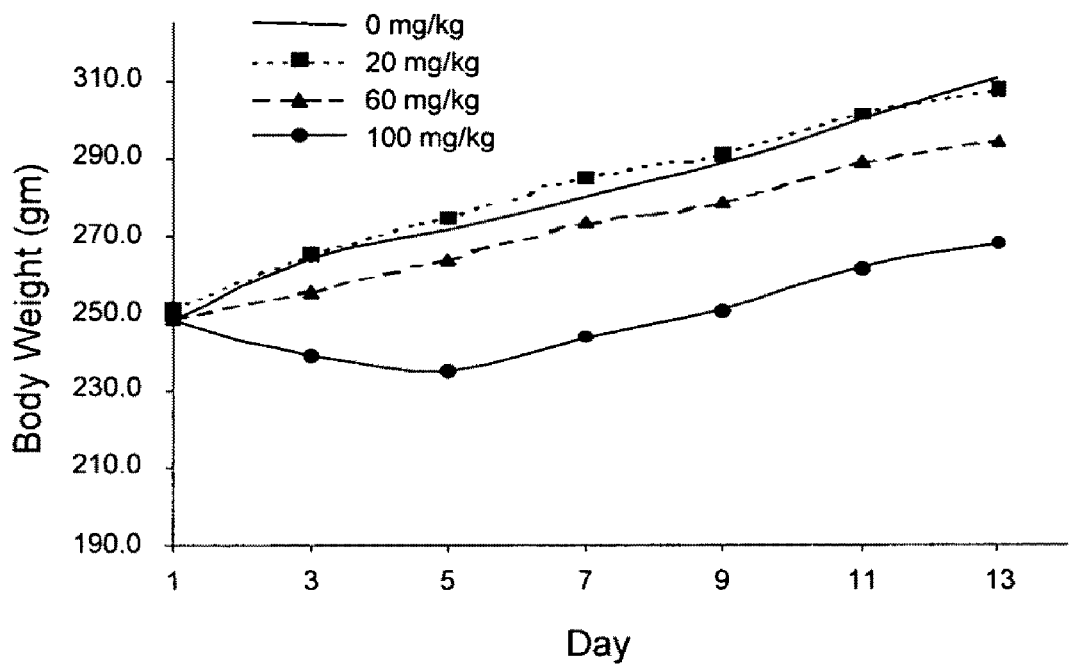
FIGS. 4A and 4B show changes in body and organ weight in animals treated with various doses of a compound of the invention.
Figure 4B:
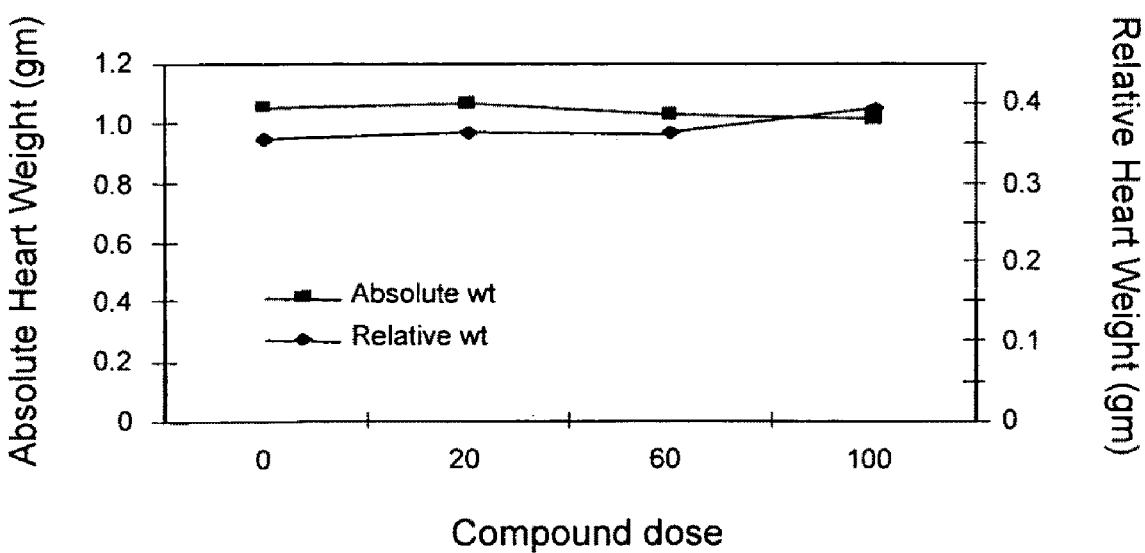

As shown in FIG. 4A, animals treated with compounds of the invention showed a dose-dependent retardation in weight gain. Examination of animals indicated that there was not a general retardation in growth, as the absolute weight of most organs in treated animals was not significantly different than the respective organ weights in control, untreated animals. For example, the absolute heart weight in animals treated with compound was essentially the same as the absolute heart weight in untreated controls (FIG. 4B). However, relative organ weight, wherein the weight of the organ is expressed as a fraction of the total body weight, was significantly different in treated animals compared to untreated controls. For example, the relative heart weight in treated animals was significantly increased compared to control animals ($p=0.036$, one-way ANOVA/Tukey's test).

Figure 5:
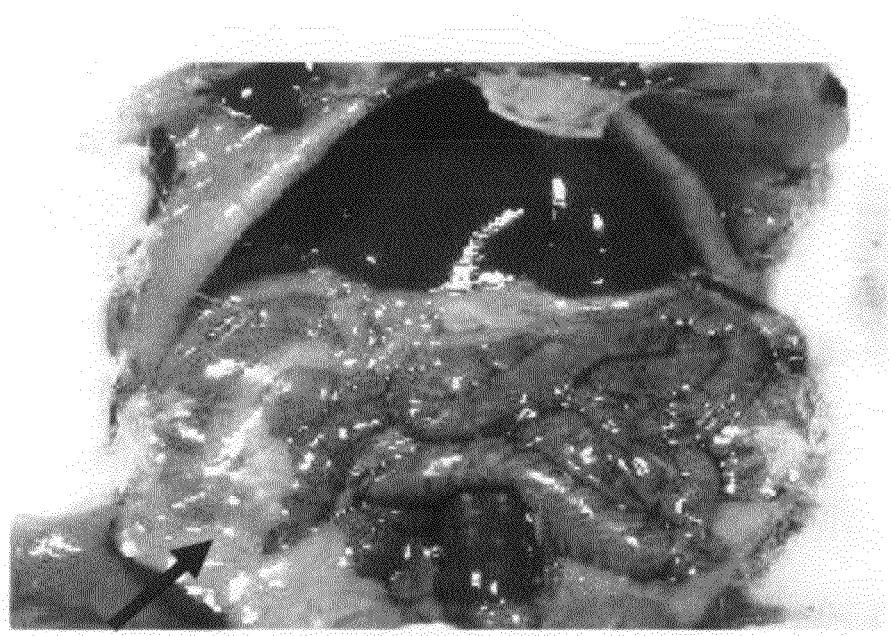
FIG. 5 shows a dose-dependent reduction in visceral fat in animals treated with a compound of the invention.
Figure 5:
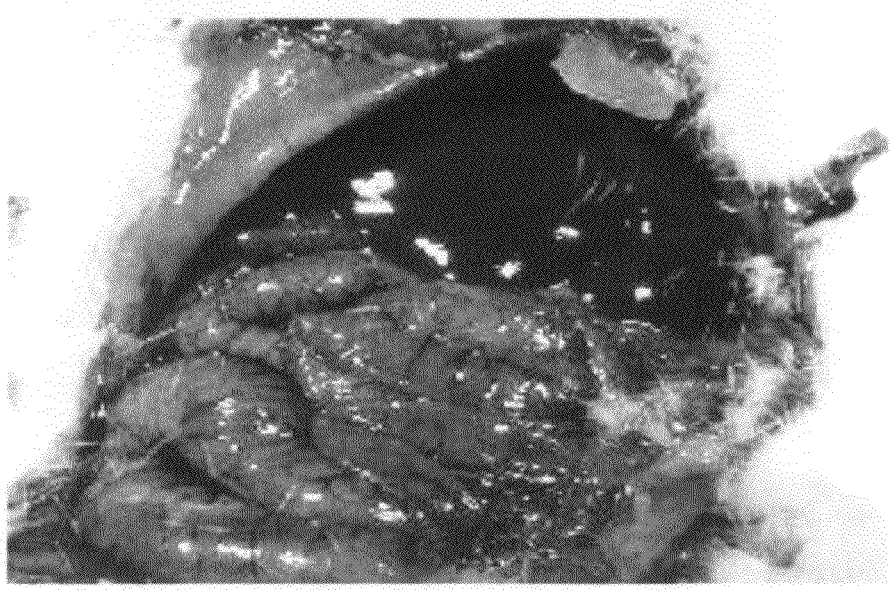

Since absolute organ weight was not significantly decreased, there was not a general growth retardation process in treated animals; however, since relative organ weight was significantly increased, there was apparently a selective loss of another tissue. As shown in FIG. 5, a dose-dependent reduction in visceral (abdominal) fat was seen in animals treated with compound. The arrow in the top panel shows visceral fat pads present in animals treated with low doses of compound, whereas the panel on the bottom shows a complete absence of fat pads in animals treated with higher doses of compound.

These results indicate that compounds and methods of the present invention can be used to regulate body weight. In particular, the present methods and compounds can be used to prevent or reduce weight gain without concomitant loss of muscle mass. The compounds and methods can be applied to modulate fat regulation, e.g., by decreasing storage of abdominal or visceral fat.

Example 6

Reduced Body Weight Gain in an Animal Model of Diet-Induced Obesity

The effect of the present compounds and methods on fat regulation, e.g., fat uptake and storage, etc., and on regulation of body weight was analyzed as follows. C57Bl/6J mice fed a high-fat diet develop severe obesity, hyperglycemia, and hyperinsulinemia, and are a model of diet-induced obesity, Type 2 diabetes, and impaired glucose tolerance. Forty male C57BL/6J mice obtained from The Jackson Laboratory (Bar Harbor Me.) were divided into the following experimental groups: Group 1: vehicle control animals fed standard mouse chow (n=10); Group 2: vehicle control animals fed high-fat mouse chow (45% fat from Research Diets) (n=10); Group 3: animals fed high-fat mouse chow and administered 75 mg/kg/day compound E by oral gavage (n=10); Group 4: animals fed high-fat mouse chow and administered 75 mg/kg/day compound A by oral gavage (n=10). The feeding regimen was continued for 28 days with weekly measurement of body weight. Animals were then sacrificed and their organs and fat pads were harvested and weighed.

Figure 6A:
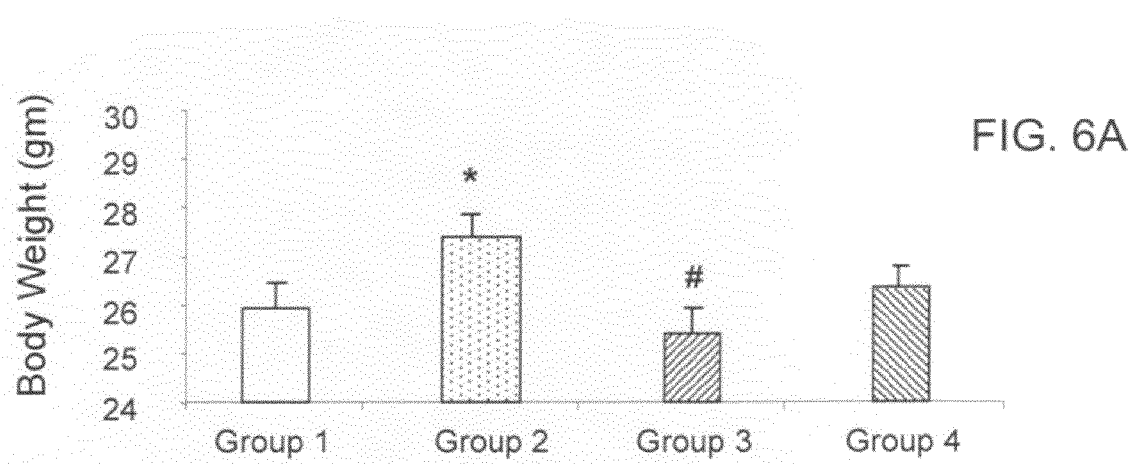
FIGS. 6A, 6B, and 6C show decreased body weight gain and abdominal fat pad weight in an animal model of diet-induced obesity upon treatment with a compound of the invention.
Figure 6B:
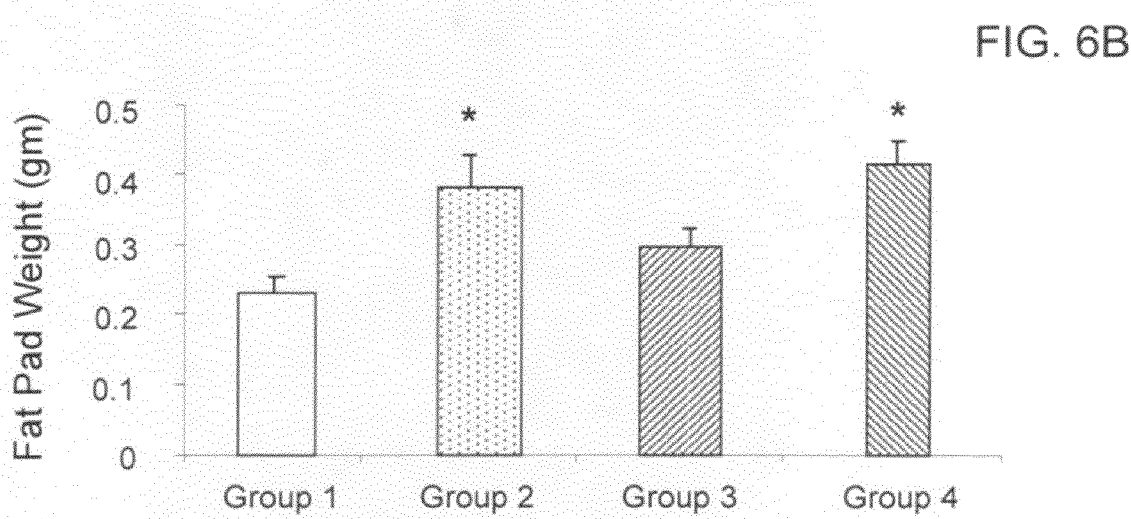
Figure 6C:
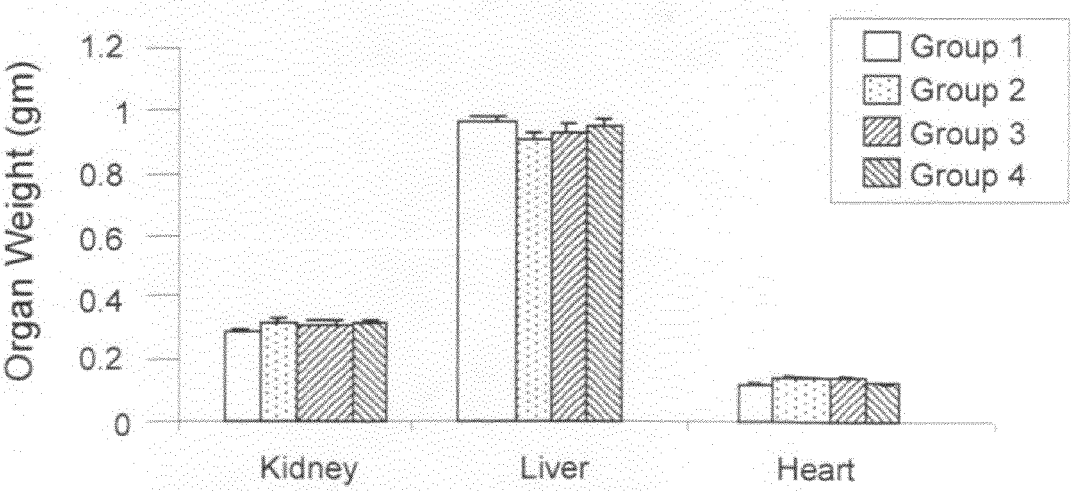

As shown in FIG. 6A, animals fed a high-fat diet (group 2) had a significantly higher body weight than animals fed standard chow (group 1) ($p<0.05$). However, animals fed high-fat diet but treated with compound E or compound A (group 3 and group 4, respectively) showed significantly less weight gain ($p<0.05$). In fact, despite the high-fat diet, animals treated with compound had essentially the same weight as animals fed a normal diet (compare group 3 and group 4 with group 1). Similarly, as shown in FIG. 6B, animals fed a high-fat diet (group 2) had a significant increase in abdominal fat pad weight compared to both animals fed standard chow (group 1) and animals fed high-fat diet that were also treated with compound of the invention (group 3 and group 4). As can be seen in FIG. 6B, animals fed the high-fat diet and treated with compound had essentially the same fat pad weight as animals fed a normal diet. FIG. 6C shows that the effect was specific to fat pad weights, as the weight of other organs including kidney, liver, and heart were essentially the same in all experimental groups.

These results indicate that observed differences in body weight between animals fed a high-fat diet with or without compound administration were specifically due to decrease in fat stores, and not due to a general decrease in growth rate. Further, the data show that treatment of animals with compounds of the invention eliminates the excessive increase in body weight associated with a high-fat diet. Further, analysis of expression profiles obtained from each group demonstrate that compounds of the invention normalize expression of genes, such as fatty acid binding protein-3 and mitochondrial uncoupling protein 1, upregulated in group 2 animals (data not shown). Thus, compounds of the invention are useful to therapeutically reduce weight gain, even under adverse dietary intake. Further, regulating weight gain by the methods and compounds of the present invention suggest that such compounds are useful to therapeutically facilitate weight loss in obese patients.

Example 7

Weight Loss in Obese Mouse

The effect of administration of compounds of the present invention on weight loss in animals is examined as follows. C57BL/6J mice are obtained from The Jackson Laboratory (Bar Harbor Me.). C57Bl/6J mice fed a high-fat diet develop severe obesity, hyperglycemia, and hyperinsulinemia, and are a model of diet-induced obesity, Type 2 diabetes, and impaired glucose tolerance. Mice are fed high-fat chow (45% of calories from fat) for 8 weeks, after which the mice are obese. Obese mice are divided into two experimental groups: Group 1 animals are control obese mice and Group 2 animals are obese mice treated with compound of the present invention. An additional group of age matched non-obese mice are also included in the study. Animals are then treated daily with compound of the invention or with vehicle control. Body weight of the mice is measured twice a week for 21 days. On day 21 the animals are weighed and then sacrificed. Abdominal fat pads, liver, kidney, and heart are isolated and weighed for analysis.

Loss of body weight upon administration of compound indicates that compounds of the invention are useful to therapeutically reduce body weight in obese patients.

Example 8

Long-Term Reduction in Serum Triglycerides

The effect of administration of compounds of the present invention on serum triglyceride levels was examined using a mouse model of diabetes as follows. Twenty male db/db mice (Harlan, Indianapolis Ind.), which carry a homozygous loss-of-function mutation in the leptin receptor, were obtained and provided with either vehicle (100 mM histidine) or compound A (0.5 mg/ml in 100 mM histidine) in drinking water ad libitum for a period of 8 weeks. Animals were then fasted overnight and blood samples were taken from the caudal vena cava under general anesthesia and placed in serum separator tubes. Blood sample analyses were performed by Quality Clinical Labs (Mountain View Calif.).

Figure 7:
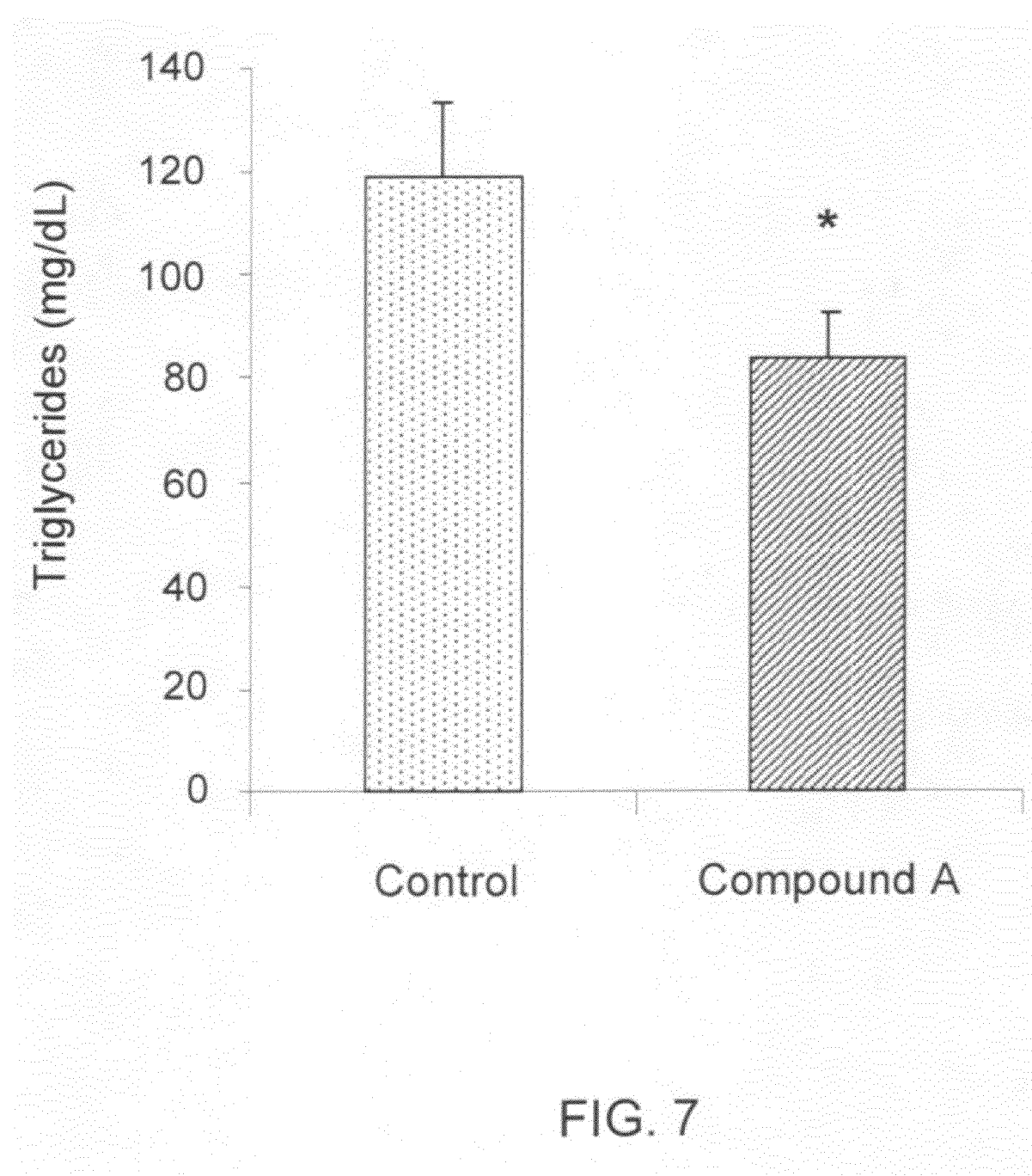
FIG. 7 shows decreased serum triglyceride levels in an animal model of diabetes when treated with a compound of the invention.

Triglycerdide levels in db/db mice are at least 1.5-2 times higher than in normal mice, and progressively increase with age. (See, e.g., Nishina et al. (1994) Metabolism 43:549-553; and Tuman and Doisy (1977) Diabetologia 13:7-11.) As shown in FIG. 7, triglyceride levels were approximately 120 mg/dL in control db/db mice at the end of the experiment. However, the triglyceride level in animals treated with compound of the invention was approximately 85 mg/dL, significantly lower than controls. Increased triglyceride levels are associated with increased risk of cardiovascular disease, and elevated triglycerides are a component of the metabolic syndrome. As the compounds and methods of the invention effectively lower or maintain triglyceride levels in conditions normally associated with elevated triglycerides, e.g., diabetes, syndrome X, macrovascular disease, or other dyslipidemias, the present methods are useful for treating individuals having or at risk of having such conditions.

Example 9

Identification of Compounds that Stabilize HIFα and Inhibit HIF Hydroxylase Activity Compounds of the present invention for use in the present methods stabilize HIFα, inhibit HIF hydroxylase activity and/or HIFα hydroxylation, etc. Thus, compounds can be identified, e.g., by their ability to stabilize HIFα. Stabilization of HIFα using compounds and methods of the present invention was examined as follows. Human cells derived from adenovirus-transformed fetal kidney epithelium (293A), cervical epithelial adenocarcinoma (HeLa), hepatocellular carcinoma (Hep3B), squamous carcinoma (SSC-25), and lung fibroblast (HLF) tissues (see, e.g., American Type Culture Collection, Manassas Va.; and Qbiogene, Carlsbad Calif.) were separately seeded into 100 mm culture dishes and grown at 37° C., 20% $O_2$, 5% $CO_2$ in media as follows: HeLa cells in Dulbecco's Modification of Eagle's Medium (DMEM), 2% fetal bovine serum (FBS); HLF cells in DMEM, 10% FBS; 293A cells in DMEM, 5% FBS; and Hep3B cells in Minimal Essential Medium (MEM), Earle's BSS (Mediatech Inc., Herndon Va.), 2 mM L-glutamine, 0.1 mM non-essential amino acids, 1 mM sodium pyruvate, 10% FBS. When cell layers reached confluence, the media was replaced with OPTI-MEM media (Invitrogen Life Technologies, Carlsbad Calif.) and cell layers were incubated for approximately 24 hours in 20% $O_2$, 5% $CO_2$ at 37° C. A compound of the invention (compound B, D, F, G, or H) or vehicle control (0.5 to 1% DMSO) was then added to existing medium, and incubation was continued overnight.

Following incubation, the cells were washed two times in cold phosphate buffered saline (PBS) and then lysed in 1 ml of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates were centrifuged at 3,000×g for 5 minutes at 4° C., and the cytosolic fractions (supernatant) were collected. The nuclei (pellet) were resuspended and lysed in 100 µl of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) were collected.

Figure 8A:
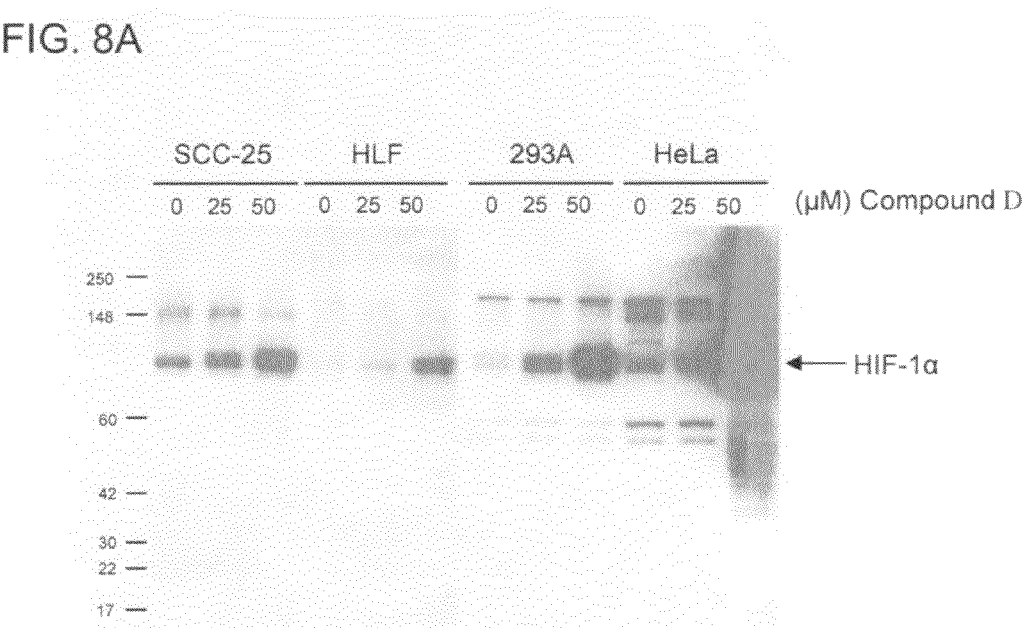
FIGS. 8A and 8B show dose-dependent HIF-1α stabilization in cells treated with compounds of the invention.

Nuclear fractions were normalized based on protein concentration and loaded onto a 4-12% TG gel and fractionated under reducing conditions. Proteins were transferred to a PVDF membrane (Invitrogen Corp., Carlsbad Calif.) at 500 mA for 1.5 hours. The membrane was blocked in T-TBS, 2% milk for 1 hour at room temperature and incubated overnight with mouse anti-human HIF-1α antibody (BD Biosciences, Bedford Mass.), diluted 1:250 in T-TBS, 2% milk. The blot was developed using SUPERSIGNAL WEST chemiluminescent substrate (Pierce, Rockford Ill.). As shown in FIG. 8A, various cell types, a representative compound of the invention (compound D) stabilized HIFα in various cell types, allowing HIFα to accumulate within the cells.

Figure 8B:
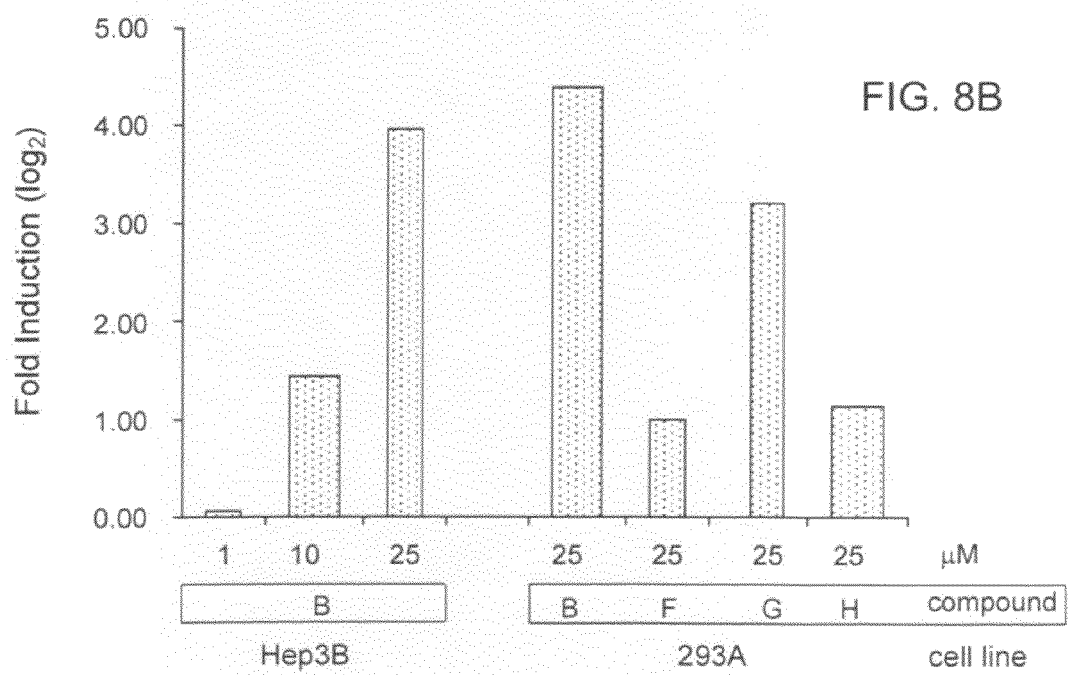

Alternatively, nuclear fractions were prepared using a nuclear extract kit (Active Motif, Carlsbad Calif.) and were analyzed for HIF-1α using a TRANSAM HIF-1 ELISA kit (Active Motif) according to the manufacturer's instructions. As shown in FIG. 8B, epithelial cells (293A) and hepatocytes (Hep3B) treated with various compounds of the invention (compounds B, F, G, and H) showed stabilization and accumulation of HIFα compared to vehicle-treated control cells.

Compounds for use in the present methods can also be identified, e.g., by their ability to modulate HIF-specific prolyl hydroxylase activity. Modulation of HIF prolyl hydroxylase activity can be identified using an assay based on the hydroxylation-coupled decarboxylation of 2-oxo-[1-$^{14}$C]-glutarate. (See Hirsila et al. (2003) J Biol Chem 278:30772-30780.) The reaction is performed in a 1.0 ml reaction volume containing 10-100 µL of detergent, e.g., Triton-X-100, solubilized cell extract obtained from cells expressing either endogenous HIF prolyl hydroxylase or a recombinant HIF prolyl hydroxylase; 0.05 µmol substrate peptide, e.g., DLD-LEMLAPYIPMDDDFQL (SEQ ID NO: 1); 0.005 mmol of $FeSO_4$, 0.16 mmol of 2-oxo[1-14C]glutarate, 2 µmol of ascorbate, 60 µg of catalase, 0.1 µmol dithiothreitol, and 50 µmol Tris-HCl buffer, adjusted to pH 7.8 at 25° C. The enzyme reaction is carried out at 37° C. for 20 minutes. The $^{14}CO_2$ produced by the reaction is captured on base-impregnated filter paper suspended in the atmosphere over the reaction mixture and counted in a scintillation counter.

Example 10

Expression of Regulatory Factors Involved in Glucose Uptake and Utilization

As the compounds and methods of the invention regulate fat metabolism, which is tightly coordinated with glucose regulation, the effect of compounds and methods on glucose uptake and metabolism was analyzed. Human SSC-25 (squamous cell carcinoma) or rat H9c2 (ventricular cardiomyocyte) cells were grown to confluence in 100 mm culture dishes at 37° C., 10% $CO_2$ in DMEM with 10% fetal calf serum. Cells were then washed twice with PBS and incubated with vehicle control, compound D (10 and 25 µM), or compound C (5, 10, and 20 µM) for 16 hours. Plates were placed on ice, culture supernatant was removed, and lysis buffer-1 (LB-1: 10 mM Tris pH 7.4, 1 mM EDTA, 150 mM sodium chloride, 0.5% IGEPAL) was added. Cells were harvested by scraping, incubated for 15 minutes on ice, and then centrifuged at 3,000×g for 5 minutes at 4° C. The supernatant, which represents the cytosolic fraction, was collected and cytosolic proteins were separated under reducing conditions using SDS-polyacrylamide gel electrophoresis (SDS-PAGE) with equal amounts of protein loaded per lane.

SDS-PAGE was conducted at 150 V for 2 hours, after which the proteins were transferred to a PVDF membrane at 400 mA for 1.5 hours at 4° C. The membrane was incubated in blocking buffer for 2 hours or overnight and washed once with T-TBS prior to addition of anti-GluT-1 antibody (Alpha Diagnostics) diluted to working concentration in blocking buffer. After overnight incubation with gentle agitation at 4° C., membranes were washed 4 times with T-TBS, followed by incubation for one hour at room temperature with conjugated secondary antibody diluted in blocking buffer. The membrane was then washed four times with T-TBS prior to development and visualization using X-ray-film and ECL SUPERSIGNAL WEST PICO chemiluminescent substrate (Pierce Chemical Co., Rockford Ill.) according to the manufacturer's instructions.

FIG. 9A shows that both compound D and compound C increased protein levels of GluT-1, a major inducible glucose transporter mediating glucose uptake, in SCC-25 and H9c2 cells, respectively. These results showed that compounds and methods of the present invention potentially increase expression of proteins involved in glucose uptake, and thus provide a therapeutic approach to enhance glucose uptake.

In a further analysis of the methods and compounds effect on glucose regulation, human 293A cells were plated confluent in 35 mm culture dishes and cultured for 1 day at 37° C., 10% $CO_2$ in DMEM containing 5% FBS and 1% penicillin-streptomycin. The media was changed to OPTI-MEM media (Invitrogen Life Technologies) and incubation was continued for an additional 18 to 24 hours. Vehicle control or compound B was then added to the media and cells were incubated for an additional 24, 48 or 72 hours. Plates were placed on ice, culture supernatant was removed, and lysis buffer-1 (LB-1: 10 mM Tris pH 7.4, 1 mM EDTA, 150 mM sodium chloride, 0.5% IGEPAL) was added. Cell lysates were harvested, cytosolic fractions were collected, and cytosolic proteins were separated using SDS-PAGE as described above. After separation, the proteins were transferred to a PVDF membrane at 400 mA for 1.5 hours at 4° C. The membrane was incubated in blocking buffer for 2 hours or overnight and washed once with T-TBS prior to addition of anti-aldolase antibody diluted to working concentration in blocking buffer. After overnight incubation with gentle agitation at 4° C., membranes were washed 4 times with T-TBS, followed by incubation for one hour at room temperature with conjugated secondary antibody diluted in blocking buffer. The membrane was then washed four times with T-TBS prior to development and visualization using X-ray-film and ECL SUPERSIGNAL WEST FEMTO or PICO chemiluminescent substrate (Pierce Chemical Co., Rockford Ill.) according to the manufacturer's instructions.

As seen in FIG. 9B, aldolase expression increased over time in cells treated with compound B for 24, 48, and 72 hours, whereas cultures treated with vehicle control showed no increase in aldolase expression. Compound B-treated cultures displayed no increases in β-tubulin expression, indicating that the increase in aldolase was specific and not associated with a generalized increase in protein expression.

These results further demonstrate that compounds and methods of the invention alter glucose regulation, and suggest that treatment with compound of the present invention potentially produce a metabolic shift in energy production via modulation of fat and glucose homeostasis.

Example 11

Increased Expression of Regulatory Factors Involved in Glucose Regulation

Figure 10A:
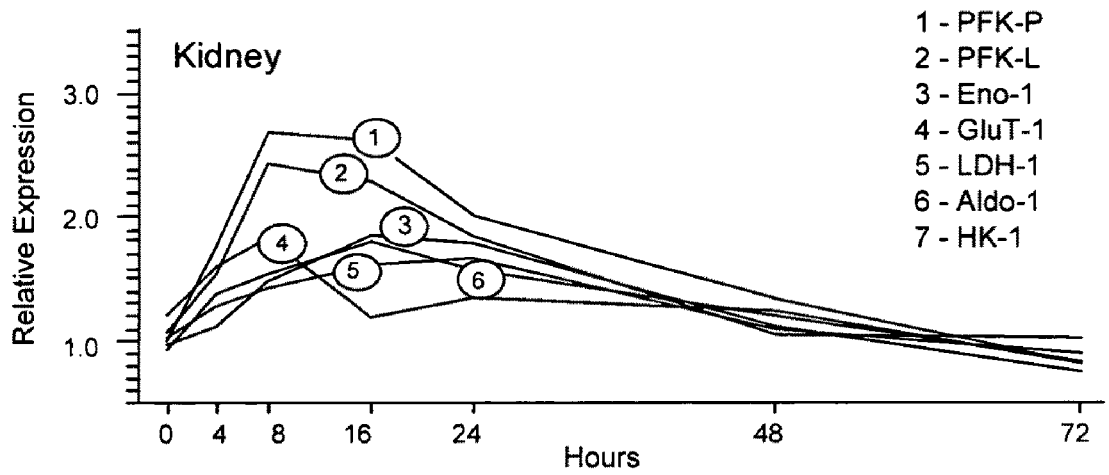
FIGS. 10A, 10B, and 10C show increase in expression of genes involved in glucose regulation in the kidney, liver, and lung, respectively, in animals treated with a compound of the invention.
Figure 10B:
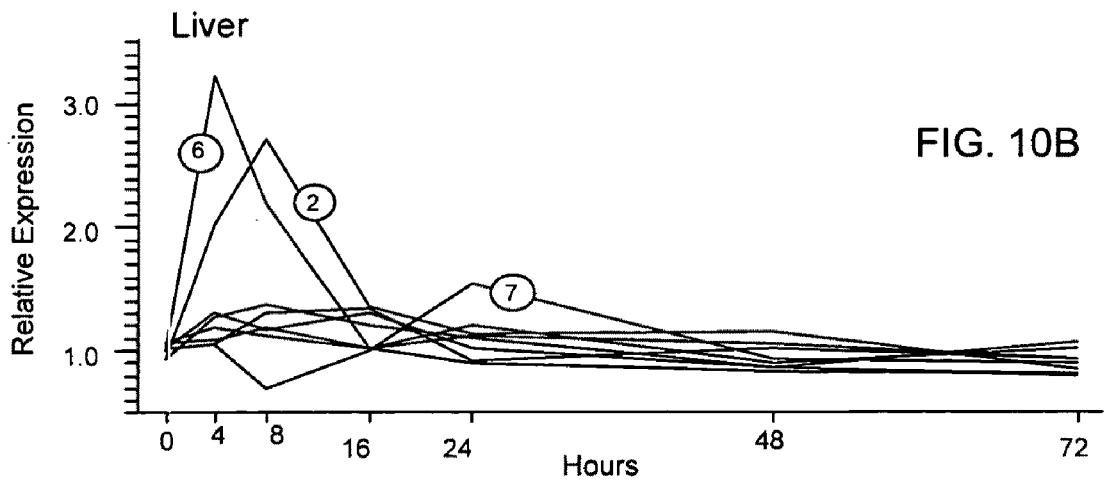
Figure 10C:
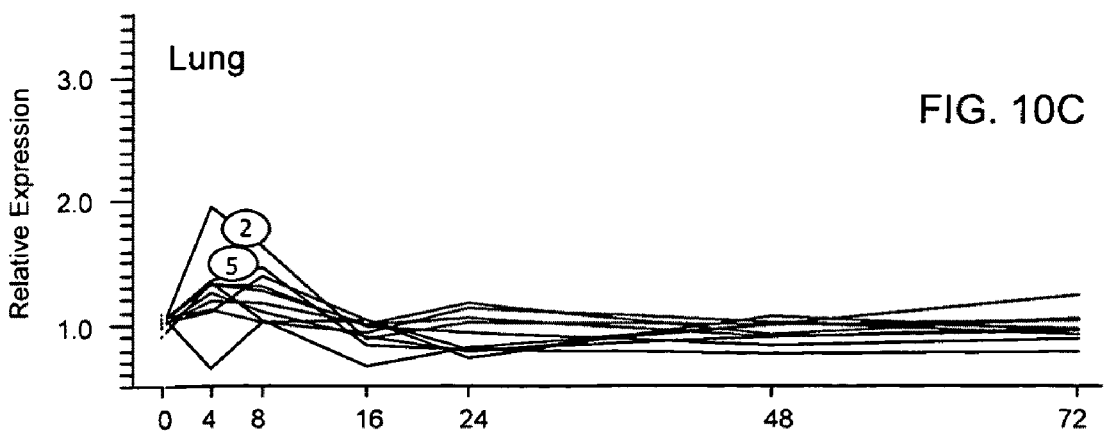

To demonstrate that the compounds and methods alter glucose uptake and utilization in vivo, samples obtained as in Example 3 above was further analyzed to identify changes in glycolytic gene induction patterns over time. As shown in FIGS. 10A, 10B, and 10C, expression of genes encoding enzymes involved in glucose regulation was increased in a coordinated fashion after treatment with compound B. Transcript patterns represented in FIGS. 10A, 10B, and 10C include platelet-type phosphofructokinase (PFK)-P (1), liver-type PFK-L (2), enolase-1 (3), glucose transporters (GluT)-1 (4), lactate dehydrogenase-1 (5), aldolase-1 (6), and hexokinase-1 (7). In the time course, most mRNA levels peaked early following administration of compound, then returned to control levels after 24 to 48 hours. Further, although expression of genes encoding glycolytic enzymes were similar between different organs, the kidney (FIG. 10A), liver (FIG. 10B), and lung (FIG. 10C) showed differences in both increases in relative expression levels and duration of the increase in particular mRNAs. These differences relate, in part, to the different degree to which glycolytic activity provides a critical source of energy for the respective tissue, especially during times of stress. These results indicated that compounds of the invention specifically induce glycolytic effects, and these effects differ by tissue.

Example 12

Effect on Oxygen Consumption

Energy production from fat and glucose generally occurs by oxidative respiration. However, under hypoxic conditions, energy utilization shifts to compensate for reduced oxygen levels. Generally, anaerobic glycolysis is increased, and fatty acid oxidation is utilized to the extent possible based on oxygen availability. Overall, the requirement for oxygen to meet net energy demands should decrease. To determine whether the methods of the invention, upon altering energy utilization, reduce cellular oxygen demand the following experiment was performed. Human 293A and HeLa cells (American Type Culture Collection) were separately grown to confluence in DMEM media containing high glucose (Mediatech, Inc., Herndon Va.) and 1% fetal bovine serum at 37° C. and 10% $CO_2$. Cells were collected and resuspended in media at a density of 500,000 cells/ml, and 0.2 ml of cell suspension was added to each well of a 96 well Oxygen Biosensor plate (BD Biosciences, Bedford Mass.). Oxygen Sensor plates (BD Biosciences) contain a ruthenium complex which is more fluorescent in the absence of oxygen. Therefore, the fluorescent read-out is increased by the presence of oxygen-consuming cells in the plate, which change the equilibrium to lower oxygen saturation and higher fluorescence.

The following treatments were added in 10 µl volumes to triplicate sets of wells: 1) 0.5% DMSO (vehicle control); 2) 200 µM sodium dodecyl sulfate (SDS; as a positive control for no oxygen consumption); 3) 5, 25, or 50 µM compound B; 4) 10, 100, or 1000 µM desferrioxamine mesylate (DFO); and 5)

media alone. Also, 0.2 ml of media alone or media with 100 mM SDS were also incubated in wells without cells to provide appropriate controls for background plate fluorescence.

Cultures were incubated for an additional 72 hours and then plate fluorescence was measured in a FL600 fluorimeter (Biotek Instruments, Inc., Winooski Ver.) at an excitation wavelength of 485 nm and emission wavelength of 590 nm. Data was plotted as a function of fluorescence and descriptive statistical analysis was performed using EXCEL software (Microsoft Corp., Bellevue Wash.).

Figure 11:
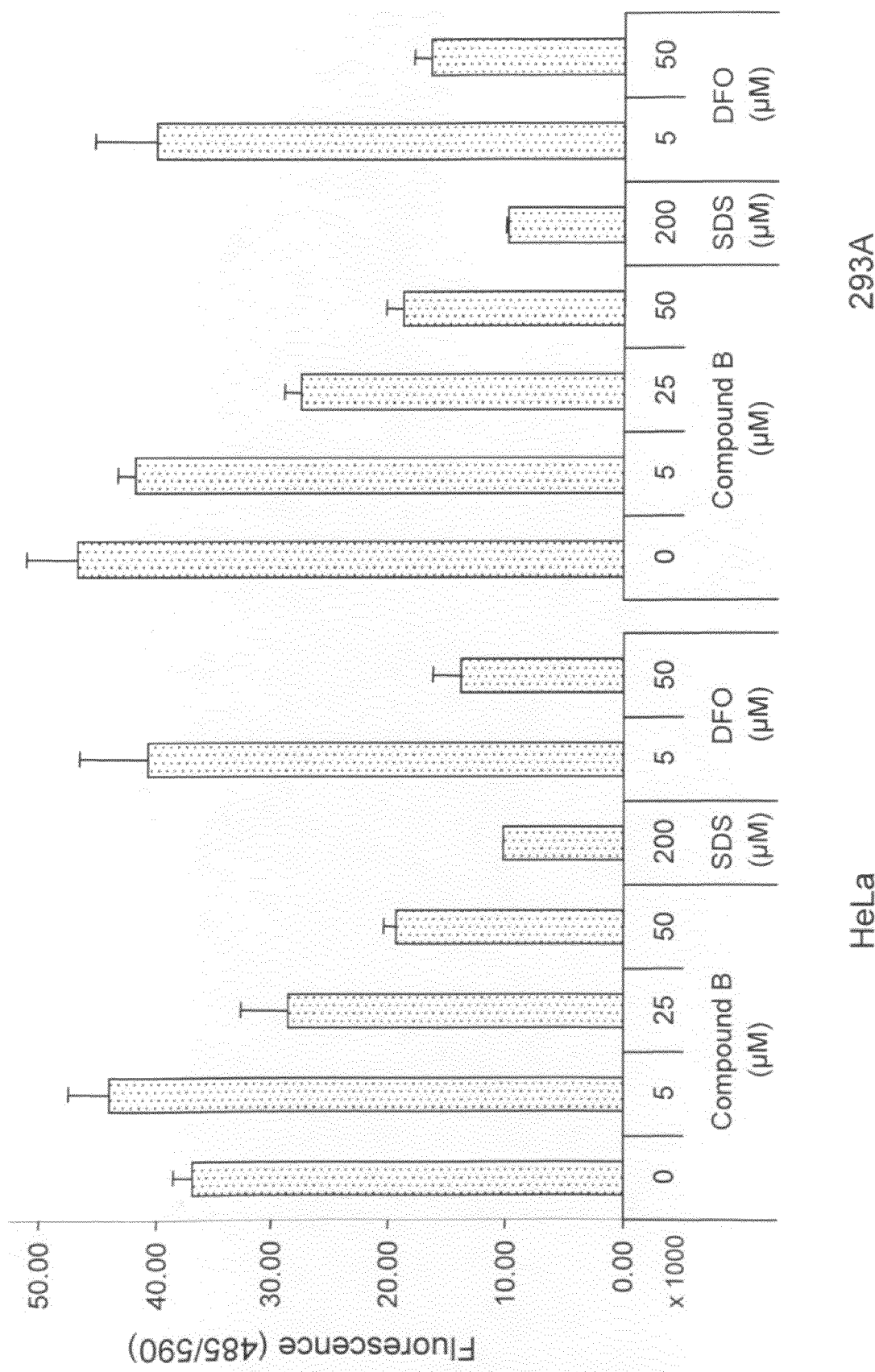
FIG. 11 shows dose response for oxygen consumption in cervical adenocarcinoma (HeLa) and transformed fetal kidney (293A) cells treated with a compound.

Both HeLa and 293A cells treated with compound of the invention displayed a dose-dependent decrease in fluorescence, indicating reduced oxygen consumption, compared to cells treated with vehicle control (see FIG. 11). The reduced oxygen consumption was not due to a loss in cellular activity or viability, suggesting possible cytotoxicity, as measured using a WST-1 colorometric assay (Roche). Additional experiments utilizing other cell types and endpoints confirmed that the decreased oxygen consumption was not associated with cytotoxicity of the compound.

The data indicate that treatment of cells of diverse tissue origin with compounds of the invention leads to shifts in cellular metabolism that reduce net oxygen consumption.

Example 13

Short-Term Increase in Plasma Triglycerides

Sprague Dawley rats were treated and samples were collected as described in Example 5. Analysis of blood samples showed that the methods of the invention produced a significant increase in plasma triglycerides at compound B doses of 60, 100 and 200 mg/kg. However, no corresponding increase in plasma cholesterol was observed. Thus, the increase in triglycerides appeared to be due to a metabolic shift toward utilization of fat stores to supply energy demand. Further, any increase in glycolysis in the absence of the oxygen-requiring TCA cycle, was potentially generating triglyceride as a byproduct.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for treating obesity in an obese subject, the method comprising administering to the subject an effective amount of a heterocyclic carboxamide compound which inhibits a hypoxia inducible factor (HIF) hydroxylase, thereby treating the obesity in the subject.

2. A method for regulating body weight in a subject in need thereof, the method comprising administering to the subject an effective amount of a heterocyclic carboxamide compound which inhibits a HIF hydroxylase, thereby regulating body weight in the subject.

3. A method for reducing body fat in a subject in need thereof, the method comprising administering to the subject an effective amount of a heterocyclic carboxamide compound which inhibits a HIF hydroxylase, thereby reducing body fat in the subject.

4. A method for reducing serum triglyceride levels in a subject in need thereof, the method comprising administering to the subject an effective amount of a heterocyclic carboxamide compound which inhibits a HIF hydroxylase, thereby reducing triglyceride levels in the subject.

5. The method of claim 3, wherein the body fat is visceral fat.

6. The method of claim 3, wherein the body fat is abdominal fat.

7. The method of any one of claim 1, 2, 3, or 4, wherein the HIF hydroxylase is a HIF prolyl hydroxylase.

8. The method of any one of claim 1, 2, 3, or 4, wherein the subject is a mammal.

9. The method of claim 8, wherein the mammal is a human.

10. The method of any one of claim 1, 2, 3, or 4, wherein the subject is a human with body mass index (BMI) between 25.0 and 29.9.

11. The method of any one of claim 1, 2, 3, or 4, wherein subject is a human with a body mass index (BMI) at or above 30.

12. The method of any one of claim 1, 2, 3, or 4, wherein the subject is a male human with a percentage body fat of greater than 25%.

13. The method of any one of claim 1, 2, 3, or 4, wherein the subject is a female human with a percentage body fat of greater than 31%.

14. The method of any one of claim 1, 2, 3, or 4, wherein the heterocyclic carboxamide compound is a quinoline carboxamide.

15. The method of claim 14, wherein the quinoline carboxamide is a quinoline-2-carboxamide.

16. The method of any one of claim 1, 2, 3, or 4, wherein the heterocyclic carboxamide compound is a quinoline carbonyl glycine.

17. The method of claim 16, wherein the quinoline carbonyl glycine is a quinoline-2-carbonyl glycine.

18. The method of any one of claim 1, 2, 3, or 4, wherein the heterocyclic carboxamide compound is an isoquinoline carboxamide.

19. The method of claim 18, wherein the isoquinoline carboxamide is an isoquinoline-3-carboxamide.

20. The method of any one of claim 1, 2, 3, or 4, wherein the heterocyclic carboxamide compound is an isoquinoline carbonyl glycine.

21. The method of claim 20, wherein the isoquinoline carbonyl glycine is an isoquinoline-3-carbonyl glycine.

22. The method of any one of claim 1, 2, 3, or 4, wherein the heterocyclic carboxamide compound a pyridine carboxamide, a pyrimidine carboxamide, a cinnoline carboxamide, or a beta-carboline carboxamide.

23. The method of claim 22, wherein the pyridine carboxamide is a 3-hydroxypyridine carboxamide.

24. The method of any one of claim 1, 2, 3, or 4, wherein the heterocyclic carboxamide compound is selected from the group consisting of a pyridine carbonyl glycine, and a pyrimidine carbonyl glycine.

25. The method of claim 24, wherein the pyridine carbonyl glycine is a 3-hydroxypyridine carbonyl glycine or a 3-methoxy pyridine carbonyl glycine.

26. The method of claim 4, wherein the compound is selected from the group consisting of [(7-Chloro-3-hydroxy-quinoline-2-carbonyl)-amino]-acetic acid, [(1-Chloro-4-hydroxy-isoquinoline-3-carbonyl)-amino]-acetic acid, [(4-Hydroxy-7-phenoxy-isoquinoline-3-carbonyl)-amino]-acetic acid, [(1-Chloro-4-hydroxy-7-methoxy-isoquinoline-3-carbonyl)-amino]-acetic acid, [(3-Hydroxy-6-isopropoxy-quinoline-2-carbonyl)-amino]-acetic acid, [(3-Hydroxy-pyridine-2-carbonyl)-amino]-acetic acid, and [(7-Benzyloxy-1-chloro-4-hydroxy-isoquinoline-3-carbonyl)-amino]-acetic acid methyl ester.

27. The method of any one of claim 1, 2, 3, or 4, wherein the heterocyclic carboxamide is a heterocyclic carbonyl glycine selected from the group consisting of a quinoline-2-carboxamide, an isoquinoline-3-carboxamide, a 3-methoxy pyridine carbonyl glycine, a 3-hydroxypyridine carbonyl glycine, and a 5-sulfonamidocarbonyl pyridine carboxylate.

\* \* \* \* \*